US009907906B2

(12) United States Patent
Ordeig et al.

(10) Patent No.: US 9,907,906 B2
(45) Date of Patent: Mar. 6, 2018

(54) SYSTEMS, METHODS, AND DEVICES FOR IN VIVO DELIVERY USING REMOTE ACTUATION OF IMPLANTABLE HYDROGEL MEMS DEVICES

(71) Applicant: The Trustees of Columbia University in the City of New York, New York, NY (US)

(72) Inventors: Olga Ordeig, Brooklyn, NY (US); Samuel K. Sia, New York, NY (US); Sau Yin Chin, Bronx, NY (US); Anne-Celine Kohler, Paris (FR); Yuk Kee Cheung Poh, Cambridge, MA (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 78 days.

(21) Appl. No.: 13/953,700

(22) Filed: Jul. 29, 2013

(65) Prior Publication Data
US 2014/0031750 A1    Jan. 30, 2014

Related U.S. Application Data

(63) Continuation-in-part of application No. 13/560,905, filed on Jul. 27, 2012.
(Continued)

(51) Int. Cl.
*A61M 5/315*     (2006.01)
*A61M 5/168*     (2006.01)
(Continued)

(52) U.S. Cl.
CPC ....... *A61M 5/16813* (2013.01); *A61K 9/0024* (2013.01); *A61M 5/14276* (2013.01); *A61M 2205/0244* (2013.01); *B82Y 5/00* (2013.01)

(58) Field of Classification Search
CPC .......... A61M 2205/0244; A61M 37/00; A61M 5/16881; A61M 5/168; A61M 5/14276;
(Continued)

(56) References Cited

U.S. PATENT DOCUMENTS 6,171,610 B1 *   1/2001   Vacanti et al. ................ 424/426
6,428,811 B1 *   8/2002   West ................... A61K 41/0028
                                                                424/497
(Continued)

FOREIGN PATENT DOCUMENTS

WO    WO 2008019434 A1 *   2/2008   .......... A61K 9/0019

OTHER PUBLICATIONS

Cheung, Yuk Kee, "Fabrication of Multi-Component Hydrogel Microstructrues and Microdevices," Doctoral Thesis, Columbia University, 2010.*
(Continued)

*Primary Examiner* — Kevin C Sirmons
*Assistant Examiner* — Tiffany Legette-Thompson
(74) *Attorney, Agent, or Firm* — Potomac Law Group, PLLC; Mark Catan

(57) ABSTRACT

MicroElectroMechanical System (MEMS) devices can be fabricated completely of hydrogel materials. Such hydrogels can include polyethylene glycol with diacrylate functional groups (e.g., PEGDA), which are photopolymerizable in the presence of crosslinkers and photoinitiators. By using PEGDA monomers of different molecular weights and at different percentages, the mechanical properties of the polymerized gels and their respective permeabilities can be tuned. This spatial variation in properties and permeabilities can lead to different functionalities between different portions of the hydrogel MEMS device. Portions of the hydrogel device may be remotely actuated by applying wave energy, for example, a magnetic field, high intensity focused
(Continued)

ultrasound, and/or infrared radiation. The remote actuation can allow the device to be actuated in vivo, for example, to allow the device to deliver a drug or other substance at a desired time and/or desired location within a patient.

14 Claims, 10 Drawing Sheets

Related U.S. Application Data

(60) Provisional application No. 61/676,849, filed on Jul. 27, 2012, provisional application No. 61/512,507, filed on Jul. 28, 2011.

(51) Int. Cl.
  A61M 5/142 (2006.01)
  A61K 9/00 (2006.01)
  B82Y 5/00 (2011.01)

(58) Field of Classification Search
  CPC ....... A61M 5/16813; A61N 1/30; B82Y 5/00; A61K 9/0024
  USPC ...... 604/19, 20, 22, 131, 500; 424/422–426; 438/49
  See application file for complete search history.

(56) References Cited

U.S. PATENT DOCUMENTS

| 7,648,619 | B2 | 1/2010 | Chaung et al. |
| 2004/0065969 | A1* | 4/2004 | Chatterjee ............... B01J 13/14 264/4.1 |
| 2007/0118215 | A1* | 5/2007 | Moaddeb ..................... 623/2.37 |
| 2007/0267011 | A1* | 11/2007 | Deem ................... A61M 29/02 128/200.23 |
| 2008/0213355 | A1 | 9/2008 | Bohmer |
| 2009/0241681 | A1 | 10/2009 | Machauf et al. |
| 2010/0068256 | A1* | 3/2010 | Bangera ............... A61K 9/0009 424/450 |
| 2010/0217312 | A1* | 8/2010 | Hill .................... A61B 17/0057 606/213 |
| 2010/0228234 | A1* | 9/2010 | Hyde et al. ................ 604/891.1 |
| 2010/0268152 | A1 | 10/2010 | Oralkan et al. |

OTHER PUBLICATIONS

Screen Capture of Publication of Cheung, Yuk Kee, "Fabrication of Multi-Compnent Hydrogel Microstructures and Microdevices," Doctorial Thesis, Columbia University, Columbia University Library, Jan. 1, 2010.*
Beebe, D.J., G.A. Mensing, and G.M. Walker, *Physics and applications of microfluidics in biology*. Annu Rev Biomed Eng, 2002. 4: p. 261-86.
Chin, C.D., V. Linder, and S.K. Sia, *Lab-on-a-chip devices for global health: past studies and future opportunities*. Lab Chip, 2007. 7(1): p. 41-57.
Quake, S.R. and A. Scherer, *From micro- to nanofabrication with soft materials*. Science, 2000. 290(5496): p. 1536-40.
Sia, S.K. and G.M. Whitesides, *Microfluidic devices fabricated in poly(dimethylsiloxane) for biological studies*. Electrophoresis, 2003. 24(21): p. 3563-76.
Vilkner, T., D. Janasek, and A. Manz, *Micro total analysis systems*. Recent developments. Anal Chem, 2004. 76(12): p. 3373-85.
Whitesides, G.M., et al., *Soft lithography in biology and biochemistry*. Annu Rev Biomed Eng, 2001. 3: p. 335-73.
Bayley, H. and P.S. Cremer, *Stochastic sensors inspired by biology*. Nature, 2001. 413(6852): p. 226-30.
Cunningham, D.D., *Fluidics and sample handling in clinical chemical analysis*. Analytica Chimica Acta, 2001. 429(1): p. 1-18.
Fu, A.Y., et al., *An integrated microfabricated cell sorter*. Anal Chem, 2002. 74(11): p. 2451-7.
Hong, J.W. and S.R. Quake, *Integrated nanoliter systems*. Nat Biotechnol, 2003. 21(10): p. 1179-83.
Grayson, A.C.R., et al., *A BioMEMS review: MEMS technology for physiologically integrated devices*. Proceedings of the IEEE, 2004. 92(1): p. 6-21.
Frost, M. and M.E. Meyerhoff, *In vivo chemical sensors: tackling biocompatibility*. Anal Chem, 2006. 78(21): p. 7370-7.
Frost, M.C. and M.E. Meyerhoff, *Implantable chemical sensors for real-time clinical monitoring: progress and challenges*. Curr Opin Chem Biol, 2002. 6(5): p. 633-41.
Voskerician, G., et al., *Biocompatibility and biofouling of MEMS drug delivery devices*. Biomaterials, 2003. 24(11): p. 1959-67.
Ainslie, K.M. and T.A. Desai, *Microfabricated implants for applications in therapeutic delivery, tissue engineering, and biosensing*. Lab Chip, 2008. 8(11): p. 1864-78.
Makamba, H., et al., *Stable permanently hydrophilic protein-resistant thin-film coatings on poly(dimethylsiloxane) substrates by electrostatic self-assembly and chemical cross-linking*. Anal Chem, 2005. 77(13): p. 3971-8.
George, P.A., B.C. Donose, and J.J. Cooper-White, *Self-assembling polystyrene-block-poly(ethylene oxide) copolymer surface coatings: resistance to protein and cell adhesion*. Biomaterials, 2009. 30(13): p. 2449-56.
Bridges, A.W., et al., *Reduced acute inflammatory responses to microgel conformal coatings*. Biomaterials, 2008. 29(35): p. 4605-15.
Alcantar, N.A., E.S. Aydil, and J.N. Israelachvili, *Polyethylene glycol-coated biocompatible surfaces*. J Biomed Mater Res, 2000. 51(3): p. 343-51.
Cruise, G.M., et al., *In vitro and in vivo performance of porcine islets encapsulated in interfacially photopolymerized poly(ethylene glycol) diacrylate membranes*. Cell Transplant, 1999. 8(3): p. 293-306.
Hoare, T. and D. Kohane, *Hydrogels in drug delivery: Progress and challenges*. Polymer, 2008.
Ratner, B.D. and S.J. Bryant, *Biomaterials: Where We Have Been and Where We are Going*. Annual Review of Biomedical Engineering, 2004. 6(1): p. 41-75.
Hennink, W. and C. van Nostrum, *Novel crosslinking methods to design hydrogels*. Adv Drug Deliver Rev, 2002. 54(1): p. 13-36.
Lee, J.W., J.H. Park, and M.R. Prausnitz, *Dissolving microneedles for transdermal drug delivery*. Biomaterials, 2008. 29(13): p. 2113-24.
Park, J.H., M.G. Allen, and M.R. Prausnitz, *Polymer microneedles for controlled-release drug delivery*. Pharm Res, 2006. 23(5): p. 1008-19.
Ryu, W., et al., *Biodegradable micro-osmotic pump for long-term and controlled release of basic fibroblast growth factor*. J Control Release, 2007. 124(1-2): p. 98-105.
Gillette, B.M., et al., *In situ collagen assembly for integrating microfabricated three-dimensional cell-seeded matrices*. Nat Mater, 2008. 7(8): p. 636-40.
Zhao, B., J.S. Moore, and D.J. Beebe, *Surface-directed liquid flow inside microchannels*. Science, 2001. 291(5506): p. 1023-6.
Duncan, R., *The dawning era of polymer therapeutics*. Nature Reviews Drug Discovery, 2003. 2(5): p. 347-360.
Cheung, Y.K., et al., *Microscale control of stiffness in a cell-adhesive substrate using microfluidics-based lithography*. Angew Chem Int Ed Engl, 2009. 48(39): p. 7188-92.
Cruise, G.M., D.S. Scharp, and J.A. Hubbell, *Characterization of permeability and network structure of interfacially photopolymerized poly(ethylene glycol) diacrylate hydrogels*. Biomaterials, 1998. 19(14): p. 1287-94.
Hwang, D.K., D. Dendukuri, and P.S. Doyle, *Microfluidic-based synthesis of non-spherical magnetic hydrogel microparticles*. Lab Chip, 2008. 8(10): p. 1640-7.
Drury, J.L. and D.J. Mooney, *Hydrogels for tissue engineering: scaffold design variables and applications*. Biomaterials, 2003. 24(24): p. 4337-51.
Cheung, Y.K., et al., *Direct patterning of composite biocompatible microstructures using microfluidics*. Lab Chip, 2007. 7(5): p. 574-9.

(56) References Cited

OTHER PUBLICATIONS

Lee, S.A., et al., *Three-dimensional fabrication of heterogeneous microstructures using soft membrane deformation and optofluidic maskless lithography*. Lab Chip, 2009. 9(12): p. 1670-5.
Albrecht, D.R., et al., *Probing the role of multicellular organization in three-dimensional microenvironments*. Nature Methods, 2006. 3(5): p. 369-375.
Tsang, V.L. and S.N. Bhatia, *Three-dimensional tissue fabrication*. Adv Drug Deliv Rev, 2004. 56(11): p. 1635-47.
Lynn, A.D., T.R. Kyriakides, and S. Bryant, *Characterization of the in vitro macrophage response and in vivo host response to poly-(ethylene glycol)-based hydrogels*. Journal of Biomedical Materials Research Part A, 2009. 9999(9999): p. NA.
Ratner, M., *Roche plans for more convenient-to-use Herceptin and Rituxan*. Nat Biotechnol. 28(4): p. 298.
Moulder, S.L., et al., *Epidermal growth factor receptor (HER]) tyrosine kinase inhibitor ZD1839 (Iressa) inhibits HER2/neu (erbB2)-overexpressing breast cancer cells in vitro and in vivo*. Cancer Res, 2001. 61(24): p. 8887-95.
Burdick, J., et al., *Controlled degradation and mechanical behavior of photopolymerized hyaluronic acid networks*. Biomacromolecules, 2005. 6(1): p. 386-391.
Mason, M., et al., *Predicting controlled-release behavior of degradable PLA-bPEG-b-PLA hydrogels*. Macromolecules, 2001. 34(13): p. 4630-4635.
Zhao, X., et al., *Active scaffolds for on-demand drug and cell delivery*. Proc Natl Acad Sci U S A. 108(1): p. 67-72.
Seiffert, S. and W. Oppermann, *Systematic evaluation of FRAP experiments performed in a confocal laser scanning microscope*. Journal of Microscopy-Oxford, 2005. 220: p. 20-30.
Grayson et al., *Differential degradation rates in vivo of biocompatible poly(lactic acid) and poly(glycolic acid) homo- and co-polymers for a polymeric drug-delivery microchip*. 2004. J Biomater Sci Polym Ed. 2004. 15(10), pp. 1281-1304.
Li et al., *In vivo release from a drug delivery MEMS device*. 2004. Journal of Controlled Release, 2004, 2(24), pp. 211-219.
Strong et al., *Hydrogel-actuated capacitive transducer for wireless biosensors*. 2002.
Yu et al., *Fabrication and characterization of a biomimetic hydrogel check valve*. 2000.
Eddington et al., *Flow control with hydrogels*.Advanced Drug Delivery Reviews 56 (2004) 199-210.
Yu et al., *Responsive biomimetic hydrogel valve for microfluidics*. 2001.
Bassetti et al., *Development and modeling of electrically triggered hydrogels for microfluidic applications*. 2005.
2nd Annu. Int. IEEE-EMBS Special Topic Conf. Microtechnologies Medicine and Biology, Madison, WI, May 2-4, 2002, pp. 410-413.
Agarwal et al., *Magnetically-driven actuation using liquid-phase polymerization (LPP) and its applications: a programmable mixer*. Proc. Hilton Head: A Solid State Sensor, Actuator, and Microsystem Workshop (Hilton Head Island, SC, USA), 2004, pp. 121-124.
Agarwal et al., "Integration of polymer and metal microstructures using liquid-phase photopolymerization," J. Micromech. Microeng., 2006, 16: pp. 332-340.
Pirmoradi et al., *On-demand controlled release of docetaxel from a battery-less MEMS drug delivery device*. Lab Chip, 2011, 11: pp. 2744-2752.
Rahimi et al., *A wireless implantable drug delivery device with hydrogel microvalves controlled by field frequency tuning*. IEEE International Conference on MEMS, 2011, pp. 1019-1022. (unable to review via web).

Lei et al, *A Hydrogel-Based Implantable Micromachined Transponder for Wireless Glucose Measurement*. Diabetes Technology & Therapeutics, 2006, 8(1), pp. 112-122.
Ziaie et al, *Hydrogel-based BioMEMS platforms for smart drug delivery*. Conf. Proc. IEEE Eng. Me. Biol. Soc., 2004, 4, p. 2670.
Cheung, Yuk Kee, *Fabrication of multi-component hydrogel microstructures and microdevices*. Doctoral Dissertation, Columbia University, Nov. 2011.
Li et al. *Gold nanocages covered with thermally-responsive polymers for controlled release by high-intensity focused ultrasound*. Nanoscale, vol. 3 (2011): 1724-1730.
De Smet, et al. *Magnetic resonance imaging of high intensity focused ultrasound mediated drug delivery from temperature-sensitive liposomes: An in vivo proof-of-concept study*. Journal of Controlled Release, vol. 150 issue 1 (2011): 102-110.
Staruch et al. *Localized drug release using MRI-controlled focused ultrasound hyperthermia*. International Journal of Hyperthermia. vol. 27 / Issue 2, pp. 156-171.
Moon et al. *A new theranostic system based on gold nanocages and phase-change materials with unique features for photoacoustic imaging and controlled release*. Journal of the American Chemical Society, col. 133, issue 13, pp. 4762-4765.
Tabatabaei, Seyed Nasr, Jacinthe Lapointe, and Sylvain Martel. "Magnetic Nanoparticles Encapsulated in Hydrogel as Hyperthermic Actuators for microrobots Designed to Operate in the Vascular Network." online], http://ieeexplore.ieee.org/xpl/freeabs_all.jsp (2009).
Maloney, John M., et al. "Electrothermally activated microchips for implantable drug delivery and biosensing." Journal of controlled release 109.1 (2005): 244-255.
Alexander et al. Microelectromechanical Drug Delivery Systems. Northwestern University, ME 381 Final Project. Dec. 3, 2004.
Elman, N. M., HL Ho Duc, and Michael J. Cima. "An implantable MEMS drug delivery device for rapid delivery in ambulatory emergency care." Biomedical microdevices 11.3 (2009): 625-631.
Voskerician, Gabriela, et al. "Biocompatibility and biofouling of MEMS drug delivery devices." Biomaterials 24.11 (2003): 1959-1967.
Hawkins, et al. A hybrid mems device for precise control of transdermal drug delivery.
Gensler, Heidi, et al. "Implantable MEMS drug delivery device for cancer radiation reduction." Micro Electro Mechanical Systems (MEMS), 2010 IEEE 23rd International Conference on. IEEE, 2010.
Richards Grayson, Amy C., et al. "Electronic MEMS for triggered delivery." Advanced drug delivery reviews 56.2 (2004): 173-184.
Backman et al. Drug Delivery. University of California, Irvine, EECS274: Lecture 13. Spring Quarter.
Gu, Yuandong, Antonio Baldi, Babak Ziaie, and Ronald A. Siegel. "Modulation of drug delivery rate by hydrogel-incorporating MEMS devices." In Microtechnologies in Medicine Biology 2nd Annual International IEEE-EMB Special Topic Conference on, pp. 406-409. IEEE, 2002.
Gardner, Phyllis. "Microfabricated nanochannel implantable drug delivery devices: trends, limitations and possibilities." (2006): 479-487.
Sbiaa, Z. "MEMS fabricated chip for an implantable drug delivery device." In Engineering in Medicine and Biology Society, 2006. EMBS'06. 28th Annual International Conference of the IEEE, pp. 5621-5624. IEEE, 2006.
Satarkar, Nitin S., Wenli Zhang, Richard E. Eitel, and J. Zach Hilt. "Magnetic hydrogel nanocomposites as remote controlled microfluidic valves." Lab on a Chip 9, No. 12 (2009): 1773-1779.

\* cited by examiner

FIG. 5C  FIG. 5D

SYSTEMS, METHODS, AND DEVICES FOR IN VIVO DELIVERY USING REMOTE ACTUATION OF IMPLANTABLE HYDROGEL MEMS DEVICES

STATEMENT REGARDING FEDERALLY SPONSORED RESEARCH

The present invention was made with U.S. Government support under grant/contract no. 0747747 awarded by the National Science Foundation, Division of Electrical, Communications and Cyber Systems (ECCS). The U.S. Government has certain rights in the invention.

FIELD

The present disclosure relates generally to polymer MicroElectroMechanical Systems (MEMS), and, more particularly, to systems, methods, and devices for fabricating and using hydrogel MEMS devices, for example, as an implantable drug delivery device.

SUMMARY

Systems, methods, and devices for micromachining MEMS devices made completely of hydrogels are disclosed herein. The hydrogels include polyethylene glycol with diacrylate functional groups (e.g., PEGDA), which are photopolymerizable in the presence of crosslinkers and photoinitiators. By using PEGDA monomers of different molecular weights and at different percentages, the mechanical properties of the polymerized gels and their respective permeabilities can be tuned. This spatial variation in properties and permeabilities can be used to provide different functionalities in respective different portions of the hydrogel device. Portions of the hydrogel device may be remotely actuated by applying wave energy to the device or the portions. For example, one or more of a magnetic field, high intensity focused ultrasound, and infrared radiation can be applied as the wave energy to effect actuation of the hydrogel portions. The remote actuation can allow the device to be actuated in vivo, for example, to allow the device to deliver a drug or other substance at a desired time and/or desired location within a patient.

Also disclosed herein is an exemplary embodiment of a hydrogel MEMS device as an implantable drug delivery device. Using a layer-by-layer photolithographic process, hydrogel MEMS device can be fabricated with impermeable depots, which can serve as fluid (e.g., drug) containing reservoirs. Additionally, a permeable window can be fabricated during the photolithographic process. Such a window may serve as an exit pathway for drug delivery via a diffusion mechanism. A hydrogel component that is movable with respect to the other hydrogel portions of the MEMS device can be provided to open/close the drug containing reservoirs. The hydrogel component can be constructed such that application of wave energy to the MEMS devices or to the hydrogel component causes displacement of the hydrogel component. The MEMS device can thus be actuated remotely to allow release of the drug from the reservoir. For example, such a hydrogel MEMS device can store and deliver molecules with a molecular weight of 150 kDa. Since the MEMS device is made entirely of a biocompatible hydrogel, it can be implanted in vivo. For example, such a hydrogel MEMS device can deliver Herceptin® (trastuzumab) (a monoclonal antibody with a size of 150 kDa) for breast cancer therapy or other drugs according to one or more treatment modalities.

In one or more embodiments, an implantable MEMS device for delivery of a substance in vivo can include first and second hydrogel structures. The first hydrogel structure can have a reservoir containing the substance therein. The reservoir can have an outlet portion. The second hydrogel structure can be within the first hydrogel structure and movable with respect thereto from a first position to a second position. The second hydrogel structure in the first position can block the outlet portion to prevent egress of the substance from the reservoir. The second hydrogel structure in the second position can allow egress of the substance from the reservoir via the outlet portion. The second hydrogel structure can have a composition such that application of external wave energy to the MEMS device causes the second hydrogel structure to move from the first position to the second position.

In one or more embodiments, an implantable MEMS device is formed of hydrogels and can include first and second hydrogels. The second hydrogel can be separate from the first hydrogel and supported thereon. The second hydrogel can be displaceable independent of the first hydrogel. The second hydrogel can be constructed such that application of external wave energy to the MEMS device causes the second hydrogel to displace with respect to the first hydrogel.

In one or more embodiments, a discrete, unattached hydrogel component can be housed in a hydrogel structure of an implantable MEMS device. An implantable MEMS device method can include displacing a discrete unattached hydrogel component from a first position in the hydrogel structure to a second position in the hydrogel structure by applying at least one of a magnetic field, high intensity focused ultrasound, and infrared radiation to the MEMS Objects and advantages of the subject matter of the present disclosure will become apparent from the following detailed description when considered in conjunction with the accompanying drawings.

BRIEF DESCRIPTION OF DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIGS. 5C-5D show a setup for remotely actuating a hydrogel MEMS gear using a magnetic field, according to one or more embodiments of the disclosed subject matter.

DETAILED DESCRIPTION

Figure 1A:
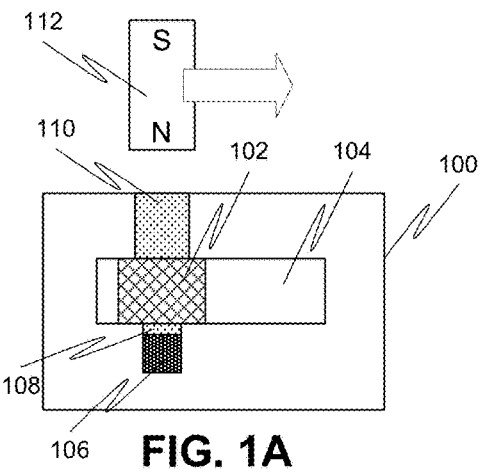
FIGS. 1A-1B are schematic diagrams showing top and side views of a hydrogel MEMS device for drug delivery in a first configuration, according to one or more embodiments of the disclosed subject matter.

In vivo MEMS and tissue engineering both deal with implantable materials of controlled composition and function, but their research have proceeded largely on separate tracks. In particular, the large array of biocompatible and biodegradable materials used in tissue engineering is distinct from the silicon-based materials used in many conventional MEMS devices. One limitation thus far is that a majority of the microfabrication technologies available for making advanced MEMS devices are incompatible with soft hydrogels that mimic native human tissues. In contrast, disclosed herein are biocompatible and biodegradable hydrogels that can be microfabricated and that can be constructed to have widely applicable functions (e.g., micropumps and microvalves) that have traditionally been associated only with conventional silicon-based MEMS devices.

Such "hydrogel micromachining" technology enables new manufacturing capabilities to bridge MEMS and tissue engineering, and can benefit both research fields via improved biocompatibility for MEMS devices, as well as active functionality for implanted tissues. For example, embodiments of a hydrogel MEMS device disclosed herein can be externally actuated even when implanted in a patient (e.g., a human or animal). However, applications for hydrogel MEMS devices microfabricated according to the teachings of the present disclosure are not limited to implantable uses. Other uses and applications for the disclosed subject matter are also possible according to one or more contemplated embodiments.

MEMS can provide powerful analytical tools for human health, such as sensing of analytes in the human body. A wide variety of complex MEMS components have been developed, including actively moving parts, flow sensors, pressure regulators, pumps, valves, mixers, and detectors. Conventionally, MEMS devices have been designed and fabricated as planar units by repeated application of micromachining steps on silicon-based materials such as thin-film deposition, photolithography, and etching. This method for design and manufacturing has worked well for ex vivo sensors.

Despite intensive work on adapting it for in vivo sensors, however, an important challenge for implantable MEMS devices is long-term biocompatibility. Implantation into a host results in accumulation of lymphocytes and formation of granulation tissue and fibrous capsule, or biofouling due to adsorption of biomolecules and the subsequent adhesion of host cells. To reduce biofouling, a strategy is to chemically modify implant surfaces with protein resistant moieties such as poly(ethylene glycol) (PEG) or oligo(ethylene glycol) terminated alkanethiols to inhibit cellular adsorption. These protein-resistant components may be coated on to the device surfaces in the form of thin films, or self-assembled monolayer. While many of these surface modifications exhibit reduced leukocyte adhesion/activation in vitro, inconsistent results have been obtained regarding the ability of these materials to reduce in vivo acute and chronic inflammatory responses.

By contrast, hydrogels can exhibit superior biocompatibility and non-fouling properties. A vast variety of hydrogels are well suited for in vivo applications. Hydrogels can also be engineered to render controlled degradability by incorporating hydrolytic labile groups or enzyme cleavable sites—a property that is lacking in conventional MEMS materials. Moreover, most hydrogels are soft and flexible, minimizing irritation and allowing conformal contact to surrounding tissues. Fabrication techniques for hydrogel devices include photolithography and micromolding. Photolithography uses light to micropattern photo-curable hydrogel (with or without masks), whereas micromolding transfers features from a master substrate to hydrogel via casting. Such techniques can be used to produce hydrogel-based devices for in vivo applications such as drug delivery, tissue engineering, and biosensing (e.g., by swelling in response to changes in osmotic pressure, pH, temperature, or analyte concentration).

Conventional micromachining techniques (e.g., thin-film deposition and etching) often involve harsh processing conditions and thus may be incompatible with hydrogels. It may therefore be impractical to employ conventional micromachining techniques to hydrogel devices in order to provide features enjoyed by semiconductor-based MEMS devices, e.g., actively moving parts that can be externally actuated, multiple aligned and spatially complex 3-D components, controllable material properties. Accordingly, presented herein is a hydrogel micromachining technique (including corresponding systems, devices, and methods) for forming a hydrogel MEMS device with the above-noted features. Such techniques can be used to form complex hydrogel devices that are biocompatible, such as a controlled drug-delivery implantable hydrogel device.

For example, poly(ethylene glycol) diacrylate (PEGDA) can be used as the hydrogel for constructing a MEMS device. PEGDA is a widely used non-toxic and non-fouling hydrogel. PEG has been approved by the U.S. Food & Drug Administration (FDA) for in vivo use in humans. PEGDA hydrogel can have tunable mechanical properties (e.g., 1 kPa to 1 MPa), permeability, and magnetic properties. In addition, PEGDA has superior in vivo biocompatibility as compared to conventional MEMS materials (i.e., semiconductor materials). PEGDA hydrogel can also be easily microfabricated and integrated to form complex 3-D microstructures. The fabrication techniques disclosed herein can be used to form MEMS devices entirely out of PEGDA hydrogel, such as, but not limited to, implantable MEMS devices, for example, as shown in FIG. 1B.

MEMS devices can be engineered with different biocompatibility profiles (e.g., degradability, immune-isolation) based on the wide set of known properties of biomaterials. For example, since degradation products from PEG-based hydrogels can be safely metabolized or excreted by the host, the entire implanted MEMS device can be triggered to initiate degradation, and the need for surgical removal of devices can be circumvented. In addition, the devices can be desiccated and later rehydrated without losing functionality. Thus, such MEMS devices can be stored in a desiccated state between fabrication and implantation into a patient.

Biodegradation of PEGDA hydrogel is possible over an implantation time period (e.g., 4 weeks in wild-type animals). Degradation of PEGDA hydrogel may be due to the presence of high levels of reactive oxygen species secreted by activated macrophages, which leads to oxidative degradation of the hydrogel. In immunodeficient animals, it may be possible for the hydrogel devices to survive with no or little degradation of the hydrogel devices over a 4-week implantation period. Implantation in immunodeficient animals may elicit a much weaker inflammatory response and hence less reactive oxygen species may be secreted as compared to wild-type animals. Where biodegradation of the hydrogel devices is desired, photopolymerizable and biodegradable hydrogels, such as, but not limited to, methacrylated hyaluronic acid and poly(lactic acid)-PEG-poly (lactic acid) copolymer, can also be used with/in the disclosed systems, methods, and devices.

TABLE 1

Comparison of Conventional MEMS machining with Hydrogel machining

| Conventional MEMS Micromachining | Hydrogel Micromachining |
| --- | --- |
| 1. Photolithography to deposit masking material for etching | 1. Use photolithography to construct monolithic hydrogel supporting structures |
| 2. Deposition of sacrificial layers and structural materials for moving parts | 2. Transfer pre-formed moving parts into supporting structures |
| 3. Etch away sacrificial layers to release moving parts | 3. Sealing device by photocross-linking preformed hydrogel layer onto opened device |
|  | 4. Extract excess hydrogel prepolymer using flow. |

The properties of hydrogels may present challenges that can be ameliorated by a fabrication strategy that is different from conventional micromachining techniques. First, most hydrogels are soft, exhibiting elastic moduli that are several orders of magnitude less than conventional MEMS materials. This property may impose a tighter constraint on forming voids with low aspect ratio (i.e., the ratio of the height to the lateral dimension of the feature) and posts with high aspect ratio. Second, since hydrogels are not suited for sacrificial etching methods, it is better suited for a bottom-up approach. Thus, free-standing components may be formed elsewhere and incorporated into the supporting structures separately. Third, unlike conventional MEMS materials, hydrogels cannot be chemically deposited, sputter coated, or etched to known thicknesses/depths.

Thickness control of hydrogel structures is dependent on the particular dimensions of the supporting structure (e.g., the pre-existing template). A fluidic chamber that has flexible height control can be used to allow exchange of different hydrogel precursor solutions and varying thickness throughout the fabrication process. Since hydrogels are permeable to water, uncrosslinked precursors that remain within voids/cavities may be removed to prevent extensive swelling of hydrogel structures due to the uptake of water via osmosis. In view of the challenges proposed by hydrogel materials, a technique for microfabricating a hydrogel can include (but is not limited to): (1) constructing the supporting structures; (2) assembling moving parts; (3) sealing the device; and (4) extracting excess materials.

Figure 1B:
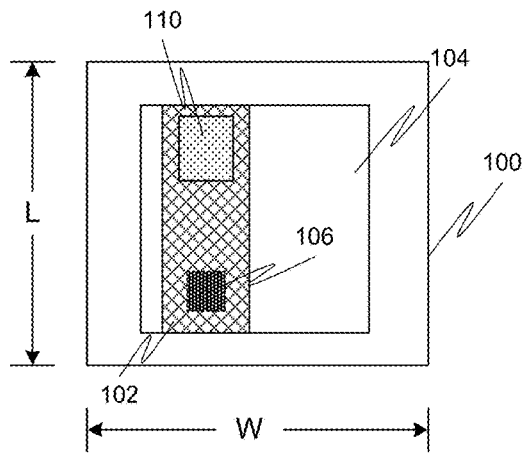

Referring to FIGS. 1A-1B, a simplified example of a hydrogel MEMS device 100 for drug delivery is shown. The hydrogel MEMS device 100 can have a structure forming a channel region 104 therein. A movable hydrogel component 102, for example, a hydrogel plug, can be enclosed within the channel region 104 and capable of independent motion therein. Accordingly, the movable hydrogel plug 102 can be displaced in the channel 104. Active remote actuation of the plug 102 can be achieved by adding super-paramagnetic particles (e.g., microbeads or nanoparticles) into the hydrogel plug 102. Remote control of the location of the plug 102 is thus accomplished by actuating the microbeads by applying a magnetic field via an ex vivo magnetic actuation setup, for example, using magnet 112. The magnet may be, for example, an NdFeB permanent magnet rod, Br max: 1.25 Tesla.

A drug can be contained in a reservoir 106 in the hydrogel MEMS device structure 100. The hydrogel regions bounding the reservoir 106 can have a permeability and/or stiffness designed to contain the drug therein. The drug may leave the reservoir 106 via an outlet portion 108 arranged adjacent to channel 104. For example, the outlet portion 108 can be a hydrogel region having a permeability that readily allows diffusion of the drug therethrough. Alternatively, the outlet portion 108 may be an opening formed in the hydrogel structure 100 adjacent the channel 104. Thus, the drug in the reservoir 106 can enter the channel 104 via the outlet portion; however, in FIGS. 1A-1B, the location of plug 102 in the channel 104 blocks egress of the drug from the reservoir.

Magnetic actuation can displace the plug 102 along the channel to a location where the outlet portion 108 of the reservoir 106 is unblocked, so as to allow diffusion 114 of the drug out of the reservoir 106. The drug thus enters the channel 104, where it can exit device 100 via a diffusion window 110 formed in the hydrogel structure 100. As with the outlet portion, the diffusion window may be a hydrogel region having a permeability that readily allows diffusion of the drug therethrough. The diffusion window 110 may be located in a region of the channel 104 remote from the reservoir 106 thereby increasing the distance drug inadvertently escaping from the plug blocked reservoir has to travel to leave the device 100. In other configurations, the diffusion window 110 may be arranged closer to the reservoir 106 or may include a larger region of the channel (for example, see FIGS. 8A-8D).

Figure 2A:
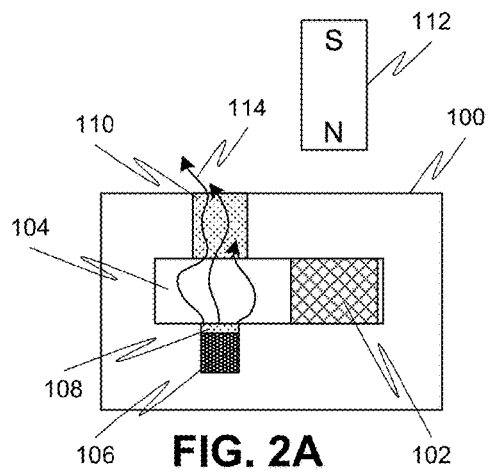
FIGS. 2A-2B are schematic diagrams showing top and side views of a hydrogel MEMS device for drug delivery in a second configuration, according to one or more embodiments of the disclosed subject matter.
Figure 2B:
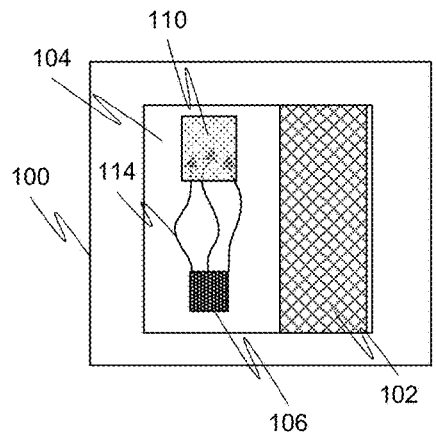

When in the closed position (FIGS. 1A-1B), the plug 102 can be in a position in the channel 104 blocking both the diffusion window 110 and the reservoir outlet portion 108. In the open position (FIGS. 2A-2B), the plug 102 can be in a position in the channel 104 that completely unblocks both the diffusion window 110 and the reservoir outlet portion 108. In other contemplated configurations for the closed position, the plug 102 may be in a position that blocks only one of the diffusion window 110 and the reservoir outlet portion 108. In other contemplated configurations for the open position, the plug 102 may be in a position that completely unblocks or at least partially unblocks one or both of the diffusion window 110 and the reservoir outlet portion 108.

The hydrogel device 100 can be on the order of millimeters (for example, having a length, L, and width, W, of 10 mm). The hydrogel device 100 can have sub-millimeter feature sizes. For example, minimum feature sizes (e.g., a width of individual components such as plug 102 or a spacing of openings such as channel 104) can be approximately 200 µm. The hydrogel devices can include one or more of the reservoirs 106 sufficient to hold an amount of fluid on the order of hundreds of nanoliters. For example, the reservoirs can hold 200 mL of fluid, which may be comparable to the capacity of silicon-based MEMS devices.

Figure 3A:
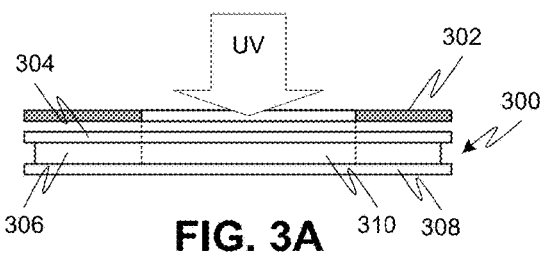
FIGS. 3A-3L show different steps in a fabrication process for a hydrogel MEMS device, according to one or more embodiments of the disclosed subject matter.

FIGS. 3A-3L illustrate a fabrication technique for creating a hydrogel component. In FIG. 3A, a microfluidic chamber 300 holds an amount of uncrosslinked hydrogel precursors in a cavity 306 between a top plate 304 and a bottom plate 308. Hydrogel prepolymers disclosed herein can be made of 10-20 w/v % PEGDA (400, 4 k or 10 kDa), 1 w/v % 12959, and 0.2 v/v % NVP in phosphate buffered saline (PBS).

Figure 4A:
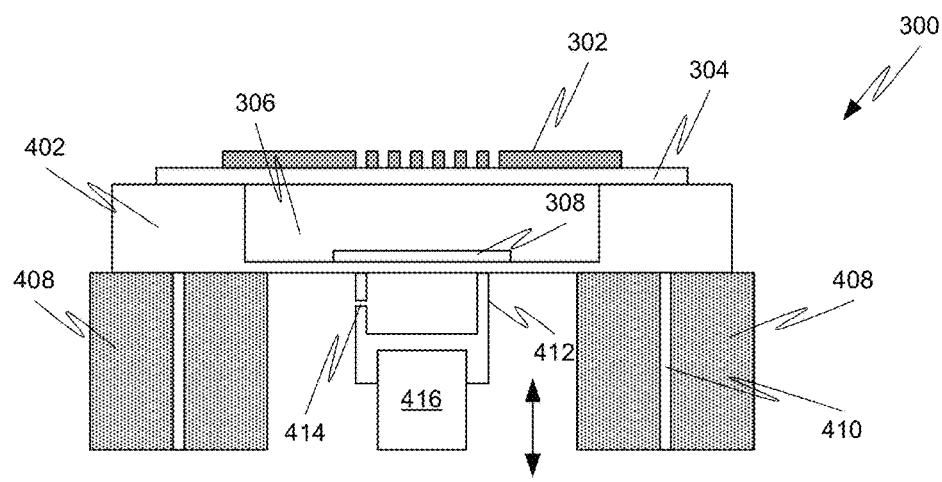
FIG. 4A is a schematic diagram showing a side view of flow through variable height lithography setup for fabricating a hydrogel MEMS device, according to one or more embodiments of the disclosed subject matter.
Figure 4B:
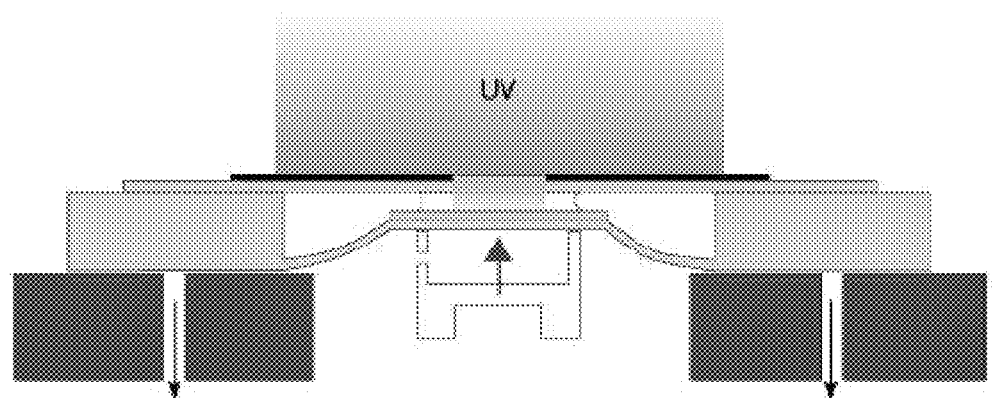
FIGS. 4B-4C are illustrations show different configurations of the lithography setup of FIG. 4A, according to one or more embodiments of the disclosed subject matter.
Figure 4C:
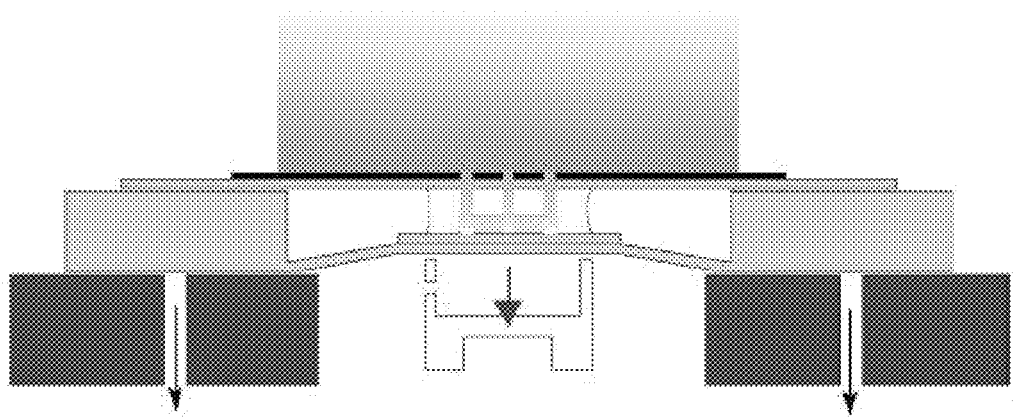

An example of such a microfluidic chamber 300 is shown in FIGS. 4A-4C. The microfluidic chamber 300 (e.g., having dimensions of 19×19×1.6 mm) can contain the hydrogel precursors and facilitate exchange of new materials and buffer washes. A flexible supporting material 402 (e.g., PDMS) supports top plate 306 and bottom plate 308 (e.g., 1 cm square cover glass, #1, 160 µm) and can provide fluidic connections for flowing gel precursors and buffer washes to/from conduits 410 in supports 408 from/to the cavity 306. Vinyl- and fluorosilane-coated glasses can be used to promote and prevent adhesion of the cross-linked hydrogel, respectively. To vary the height of the cavity 306, the microfluidic chamber 300 can be mounted on a z-axis stage 412 that changes the height of the cavity 306 in precise steps (e.g., ±2.5 µm) using displacement mechanism 416 (e.g., a micrometer). The microfluidic chamber 300 can be secured onto the stage 412 by vacuum applied via port 414.

The chamber height can be controlled through movement of the center chuck, as shown in FIGS. 4B-4C, so as to control a thickness of the hydrogel components formed. The chuck can be moved upwards using the control of a micrometer screw gauge to give the desired thickness of the hydrogel layer. Following ultraviolet (UV) exposure, the top glass coverslip can be removed and excess uncrosslinked polymer can be removed using vacuum suction or wicked away using filter paper. A different hydrogel can then be added and the chuck moved downwards to fabricate another layer of hydrogel structures.

Figure 3G:
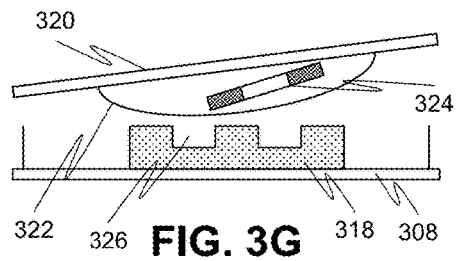
Figure 3B:
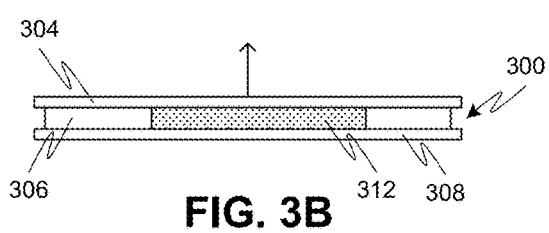
Figure 3L:
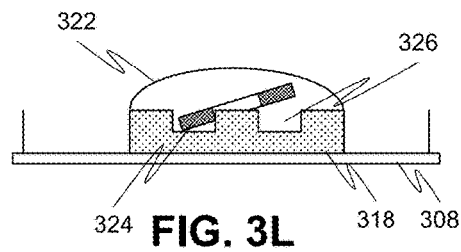
Figure 3C:
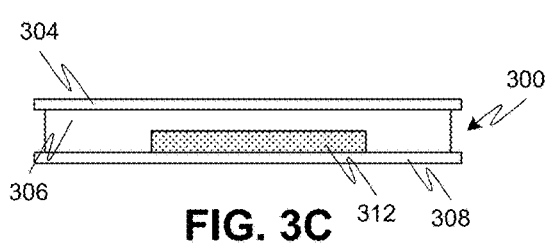
Figure 3H:
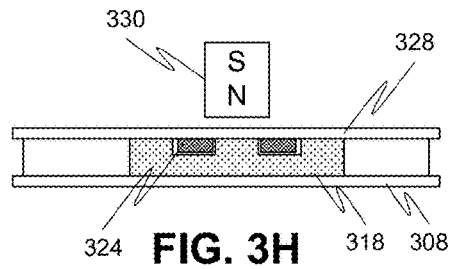

Referring again to FIG. 3A, a mask 302 disposed over the microfluidic chamber 300 can be used block portions of UV light from reaching the precursors held in cavity 306. The portion 310 of the precursors in cavity 306 exposed to the UV light cross-link to form hydrogel portion 312, as shown in FIG. 3B. The thickness of the hydrogel portion 312 can be defined by the depth of the cavity 306, i.e., the spacing between the top plate 304 and the bottom plate 308. The top and/or bottom plates can be displaced with respect to each other to increase the depth of the cavity 306, as shown in FIG. 3C.

Figure 3D:
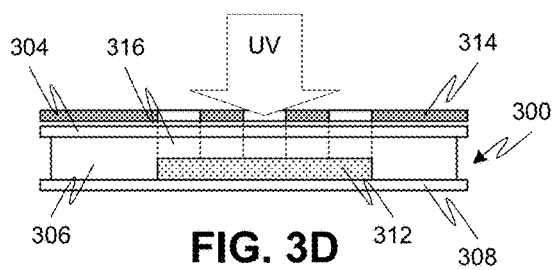

Additional hydrogel precursors can then be provided to the increased depth cavity 306, where the UV lithography using a new mask 314 can be used, as shown in FIG. 3D. Regions 316 exposed to the UV region can cross-link and polymerize to form a unitary structure 318, as shown in FIG. 3E. Additional structures using the same or different hydrogel precursors can be added using the same techniques in a step (i.e., increase cavity thickness) and repeat type process.

Figure 5A:
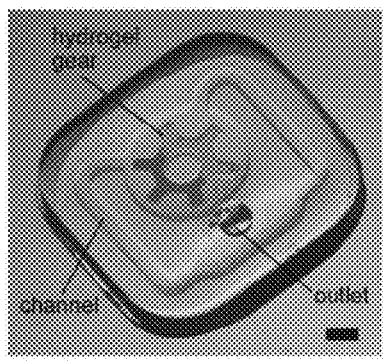
FIGS. 5A-5B are images showing a fabricated hydrogel MEMS gear, according to one or more embodiments of the disclosed subject matter. Scale bar represents 1 mm.
Figure 5B:
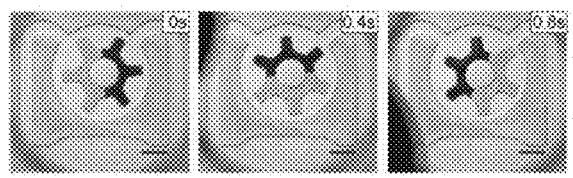

Hydrogel structure 318 can have a recess 326 for receiving a separate hydrogel component therein. For example, a magnetically actuatable hydrogel component 324 can be added to the recess 326, as shown in FIG. 3G. For example, the hydrogel component 324 can be a rotatable gear, as shown in FIGS. 5A-5B, which can be actuated using an external magnetic field produced by the setup of FIGS. 5C-5D.

A plate 320 having the hydrogel component 324 thereon, for example, held to the plate 320 using a drop of fluid 322 can be arranged over the recess 326. Contact of the drop 322 with the hydrogel structure 318 may result in transfer of the drop 322 and the hydrogel component 324 therein to the hydrogel structure 318, as shown in FIG. 3L. Alignment of the hydrogel component 324 in the recess 326 may be achieved by using magnetic actuation from, for example, magnet 330, while plate 328 prevents inadvertent removal of the component 324 from the recess 326.

Figure 3I:
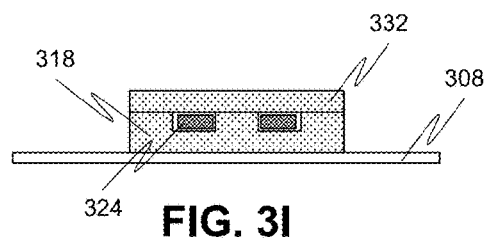
Figure 3E:
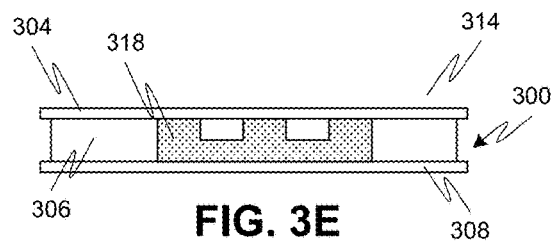

To seal the component 324 within the recess 326 another hydrogel layer 332 may be added atop structure 318, as shown in FIG. 3I. Further cross-linking may be achieved between the layer 322 and structure 318 to form a new unitary hydrogel structure 334 with the hydrogel component 324 contained therein and movable with respect thereto. For a hydrogel device that has openings connecting to the surrounding medium, the extraction of unpolymerized prepolymer from recess 326 can be easily accomplished via diffusion. However, in situations where the recess 326 is completely sealed off from the external environment, and the pore size of the bulk hydrogel is too small for the uncrosslinked materials to diffuse away, additional steps can be taken to remove the uncrosslinked materials from the inner space of the hydrogel device. If not removed, the uncrosslinked hydrogel precursors remaining in recess 326 may negatively impact subsequent device performance, for example, by swelling and deforming/damaging the hydrogel device.

Figure 3J:
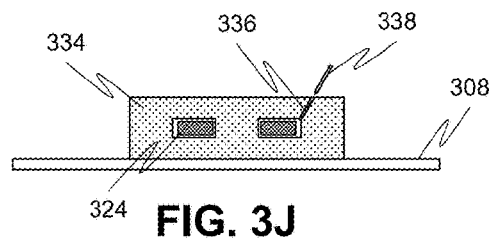
Figure 3F:
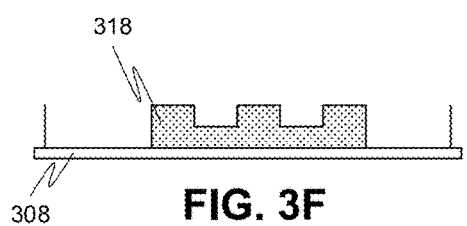
Figure 3K:
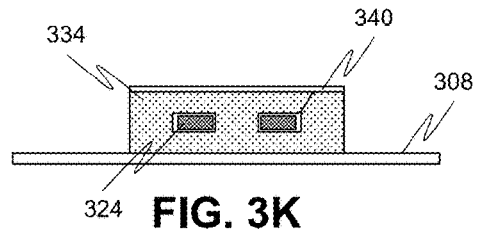

As shown in FIG. 3J, a needle 328 (e.g., a 21G needle) can be inserted through hydrogel structure 334 to form channel 336. The structure 334 can then be left in buffer solution for a period of time, for example, overnight. The channel 336 can allow for the diffusion of unpolymerized gel out of the device and the diffusion of water into the device, hence exchanging excess material for buffer solution. Since the channel 336 is relatively small it can "self-heal" as the hydrogel material itself will swell slightly and the puncture site will close on itself, as shown in FIG. 3J. This creates a temporary seal that allows for application of a final coat 340 of hydrogel prepolymer to seal off any openings without any prepolymer entering the device prior to a last cross-linking step (e.g., ultra-violet (UV) exposure).

Using the technique of FIGS. 3A-3L, a micro-gear pump was formed completely out of hydrogel, as shown in FIGS. 5A-5B. In order to achieve rotational control of the gear pump using an external magnet, half of the hydrogel gear can be doped with super-paramagnetic particles while the other half can be doped with green fluorescent microbeads (e.g., to aid in visualization of the gear movement in vivo). The permanent magnet can be connected to a slow-spinning motor and used to control the rotational motion of the hydrogel gear pump, for example, using the setup in FIGS. 5C-5D. As shown in FIG. 5B, the hydrogel gear can rotate steadily as the external magnet revolves about its axle. The rotational rate of the hydrogel gear may be controlled precisely (e.g., from 3.7 to 18.7 rpm) by varying the rotational speed of (or the voltage applied to) the motor. PEG-DA incorporated with fluorinated monomers with diacrylate groups (1H,1H,6H,6H-Perfluoro-1,6-hexyl diacrylate) can be used for moving components in order to decrease the static friction between the moving components and allow for more robust actuation and movement.

Host response is key to the success of any implantable MEMS devices. Failure can result from excessive host cells infiltration and prolonged inflammatory responses. Histological studies on the tissue surrounding the hydrogel micro gear pump (made from 10 w/v % PEGDA hydrogel) after implantation for 5 days and 4 weeks show that a hydrogel MEMS device does not elicit undesirable tissue responses. Samples from 20 w/v % PEGDA hydrogel were also fabricated and implanted for comparison. For each sample, hematoxlin and eosin (H&E) staining to evaluate the overall foreign body response and Masson's Trichrome staining to evaluate the degree of collagen deposition and fibrous capsule formation were performed (see FIG. 6).

For in vivo characterization, a small incision (e.g., <1 cm) can be made near the hind limb of a euthanized male nude mouse. A subcutaneous pocket can be made near the incision. A hydrogel micro-gear pump can be implanted into the subcutaneous pocket using a spatula. The animal and the magnetic actuation setup can be placed inside of an in vivo imaging system (e.g., a CRi Maestro imaging system), where the in vivo rotational motion of the hydrogel micro-gear can be imaged using multispectral imaging.

Hydrogel micro gear pumps can be equilibrated in PBS supplemented with 1% Penicillin-Streptomycin at 4° C. for 24 hours prior to implantation. 9-week-old, athymic male nude mice can be anesthetized with isoflurane, and two subcutaneous pockets can be made to the left and right of one midline incision (e.g., approximately 1 cm long) in each mouse. Each mouse can receive two hydrogel samples, one in each subcutaneous pocket. Incisions can be closed with sutures. Host response of two hydrogel compositions (10 and 20 w/v % of PEGDA) can be tested at two time points (5 days and 4 weeks), using one mouse per test condition. At the end of each time point, the animal can be euthanized with $CO_2$ inhalation. Hydrogel sample and surrounding tissues can be retrieved for histological analysis. The extracted surrounding tissues can be immediately fixed in 10% formalin for 48 hours. Fixed samples can be dehydrated with a graded ethanol series, embedded in paraffin, and sectioned (e.g., 5 μm thick). Sectioned tissues can be stained with H&E or Masson's trichrome. The sections can be examined for the presence of inflammatory cells and the degree of formation of fibrous capsule around the implants.

Figure 6:
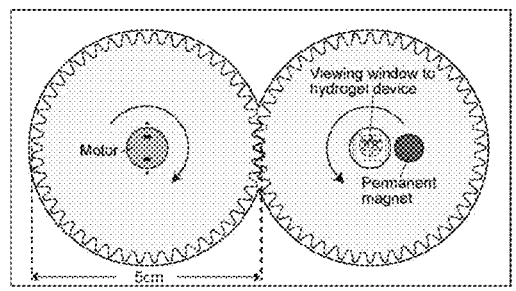
FIG. 6 shows photographs of different hydrogel devices explanted after implantation within mice, according to one or more embodiments of the disclosed subject matter. Scale bars are 500 μm.
Figure 6:
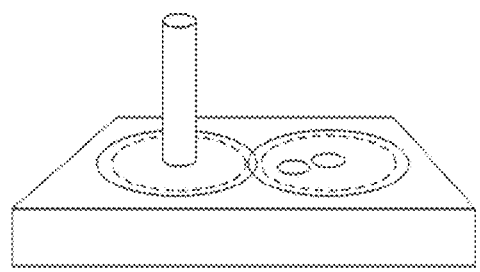
Figure 6:
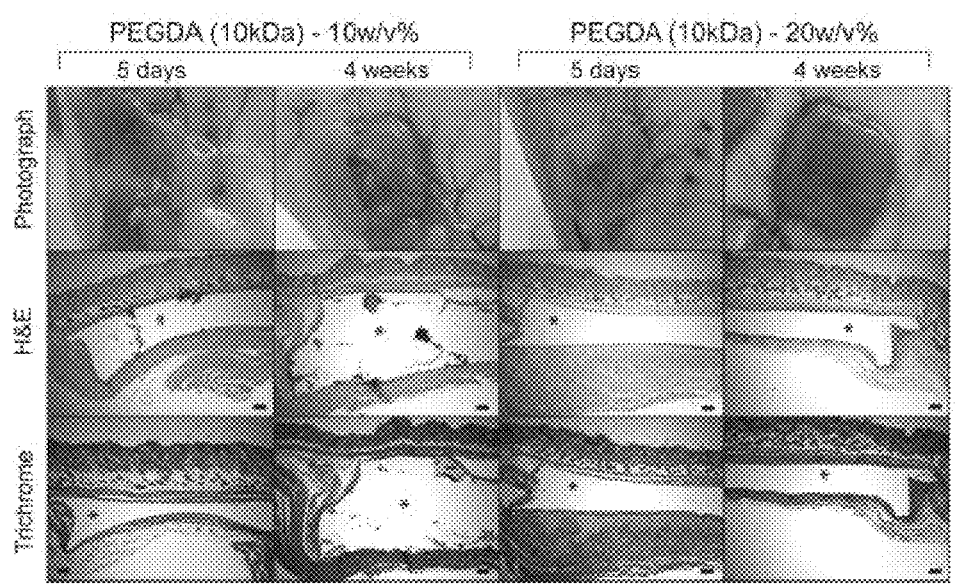

FIG. 6 shows photographs of hydrogel micro-gear pumps explanted after implantation in male nude mice after 5 days and after 4 weeks. After 5 days of implantation, both implants (10 and 20 w/v %) showed a dense accumulation of inflammatory cells at the implant interface. The response in the 20% hydrogel appeared to be more prominent than that in the 10% hydrogel. Fibrous capsules were also beginning to form around both samples, as indicated by a thin layer of collagen between the layer of inflammatory cells and muscle fibers. After 4 weeks, only a thin layer of inflammatory cells remained at the implant interface for the 10% hydrogel, whereas a thicker layer of inflammatory cells persisted at the implant interface for the 20% hydrogel. Thus, the degree of fibrous capsule formation in devices made from 20 w/v % PEGDA is more prominent than that in devices made from 10 w/v % PEGDA. In both samples, stable fibrous capsules had formed completely around the devices (indicated by the dark blue layer of fibers and layers of fibroblasts), indicating a normal healed response.

Material selection for the various components of the MEMS device can be important aspect of the hydrogel MEMS device design, especially when the device is intended for in vivo implantation into a patient for drug delivery. Mechanical stiffness of the hydrogel components, whether designed to be moving or static, is one of the criteria for selecting a gel composition for the fabrication of the device moving components. For example, a stiffness mismatch may be necessary to generate sufficient deformation during movement of a hydrogel component, whereas a more stiff hydrogel material may be necessary for exterior surfaces of the device. Compression tests were performed on the hydrogels to determine their mechanical stiffness using an Instron mechanical testing machine. Disks of 1-inch diameter and 2 mm thick were fabricated and a strain of 20% was applied to each gel disk. A wide range of stiffnesses can be achieved by varying the length of the PEG chain as well as the concentration (w/v %) of PEG used.

TABLE 2

Hydrogel Mechanical Testing Results.

| Type of Hydrogel | Composition | Mechanical Testing (kPA) | | |
|---|---|---|---|---|
| | | 1 day | 9 days | 14 days |
| 4k400 | 10% PEG4k-DA + 5% PEG400-DA | 382.6 | 343.4 | 291.9 |
| 10k5 | 5% PEG10k-DA | 19.8 | 19.8 | 16.4 |
| 20k5 | 5% PEG20k-DA | 14.7 | 13.4 | 12.4 |

TABLE 3

Hydrogel Diffusion Testing Results.

| Type of Hydrogel | Diffusion Coefficient ($cm^2/s$) | | |
|---|---|---|---|
| | 3 kDa dex | 20 kDa dex | 155 kDa dex |
| 4k400 | $4.7 \pm 0.8 \times 10^{-7}$ | $1.0 \pm 0.1 \times 10^{-7}$ | Below limit of detection |
| 10k5 | $1.2 \pm 0.2 \times 10^{-6}$ | $5.9 \pm 0.9 \times 10^{-7}$ | $8.7 \pm 1.1 \times 10^{-8}$ |
| 20k5 | Above limit of detection | $5.3 \pm 0.9 \times 10^{-7}$ | $2.5 \pm 0.5 \times 10^{-7}$ |

TABLE 4

Hydrogel Construct Release Testing Results.

| Type of Hydrogel | Percent Mass Released (%) | | |
|---|---|---|---|
| | 3 kDa dex | 20 kDa dex | 155 kDa dex |
| 4k400 | 63.4 ± 5.4 (t = 31 days, n = 8) | 28.3 ± 5.2 (t = 33 days, n = 7) | 6.0 ± 0.9 (t = 49 days, n = 7) |
| 10k5 | 71.3 ± 6.8 (t = 34 days, n = 7) | 36.8 ± 9.5 (t = 15 days, n = 6) | 18.1 ± 2.6 (t = 20 days, n = 2) |
| 20k5 | 78.4 ± 16.5 (t = 34 days, n = 4) | 79.2 ± 9.6 (t = 21 days, n = 8) | 50.6 ± 1.7 (t = 31, n = 3) |

In general, hydrogels may be porous and relatively permeable, such that small molecules are able to diffuse therethrough. Such a feature may suggest against their use for in vivo drug delivery. However, appropriate selection of the permeability of hydrogel materials in the construction of the MEMS device can prevent or at least reduce escape of a drug to be contained by the MEMS device. For example, the hydrogel that lines the reservoir in which the drug is contained should be relatively impermeable to the drug. On the other hand, a different hydrogel composition that is permeable to the drug can be selected for the access point (i.e., the outlet portion of the reservoir) through which the drug diffuses. The permeability of the hydrogel can be tuned based on PEG chain length, such that decreasing PEG chain length results in a decrease in hydrogel permeability. The reservoirs containing the drug can thus be fabricated from, for example, a 4k400 hydrogel.

Figure 7A:
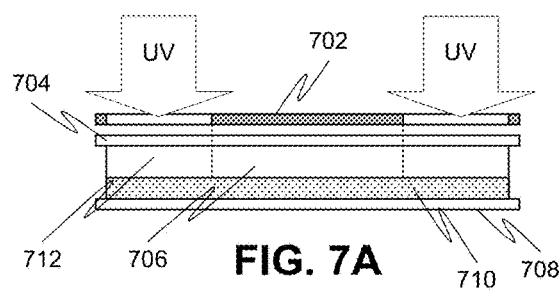
FIGS. 7A-7F show different steps in a fabrication process for constructs with enclosed reservoirs, according to one or more embodiments of the disclosed subject matter

In order to characterize the permeability of the gels used, several experiments were performed to measure the diffusion of fluorescently labeled dextran molecules out of and through the gels. A fabrication technique for forming enclosed reservoirs of a drug or drug surrogate for testing is shown in FIGS. 7A-7F. In FIG. 7A, a bottom layer 710 of hydrogel (e.g., 200 μm thick) can be formed in cavity 706 between top plate 702 and bottom plate 708, for example, using the method described with respect to FIGS. 3A-3L. Mask 702 can regulate the UV exposure of hydrogel precursors in cavity 706, such that regions 712 are cross-linked to form a unitary structure 714, as shown in FIG. 7B. For example, the unitary structure 714 may form a frame having a height of 700 μm. In FIG. 7C, a preformed slab 722 of hydrogel (e.g., 200 μm thickness) on plate 720 (e.g., a glass coverslip) can be provided within cavity 716 over hydrogel structure 714. Additional uncrosslinked hydrogel precursor can be added to the cavity, wherein portions 724 exposed to UV light passing through mask 718 become crosslinked.

Figure 7D:
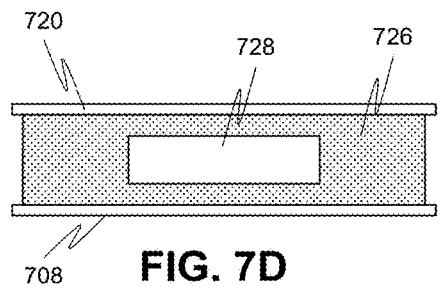
Figure 7B:
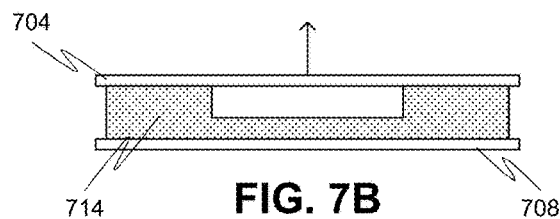
Figure 7E:
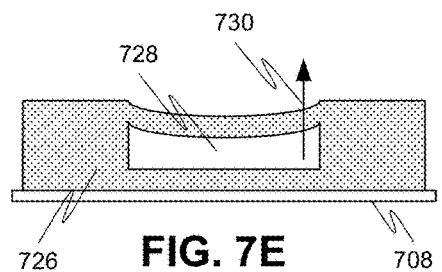
Figure 7C:
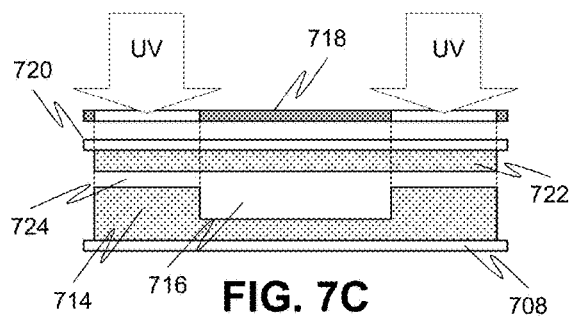
Figure 7F:
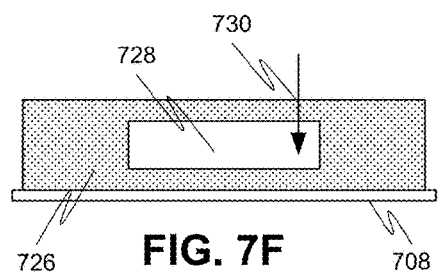
Figure 8A:
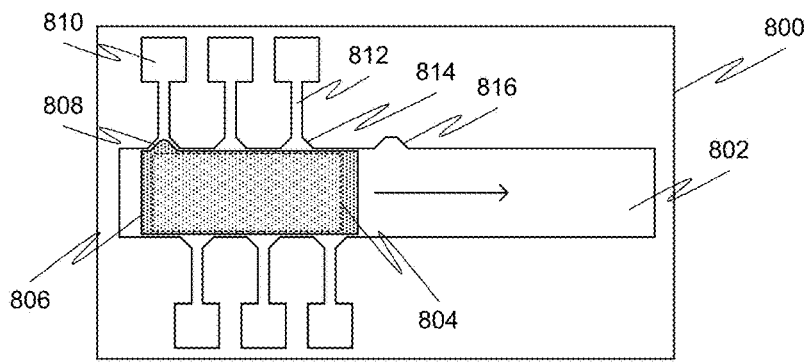
FIGS. 8A-8D are schematic diagrams showing a top view of a magnetically actuatable hydrogel MEMS device for drug delivery during different stages of actuation, according to one or more embodiments of the disclosed subject matter.
Figure 8B:
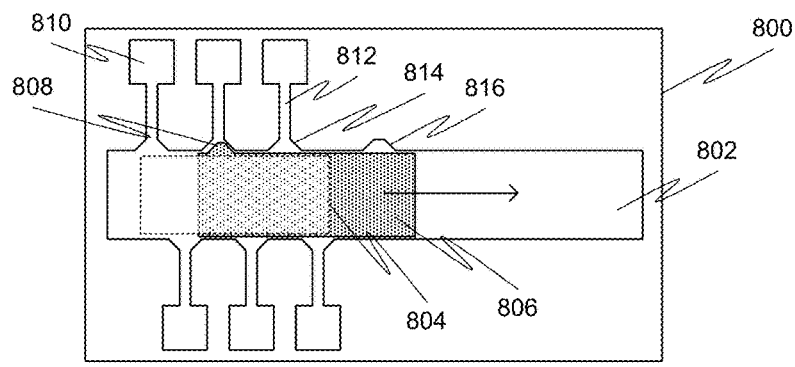
Figure 8C:
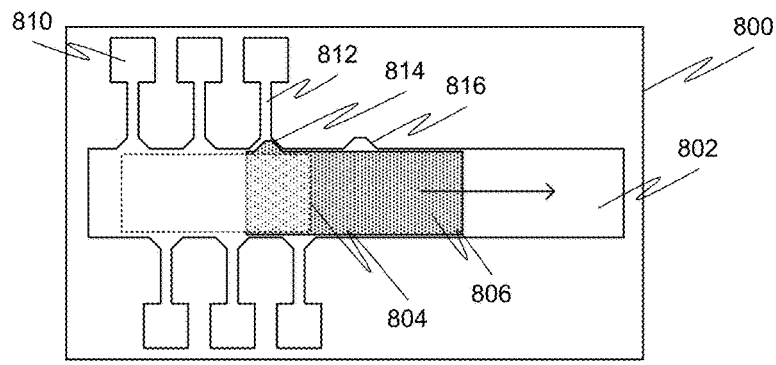
Figure 8D:
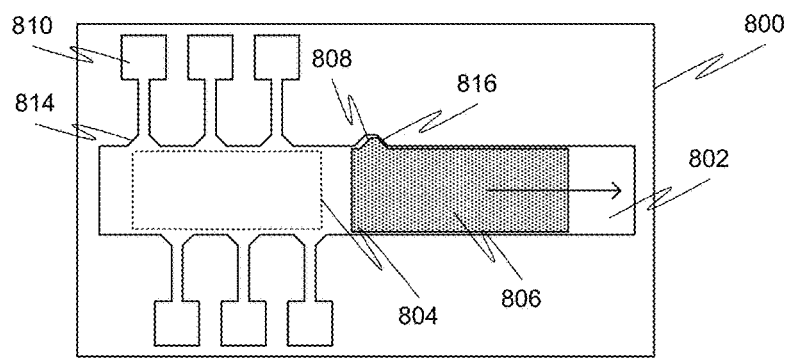
Figure 9A:
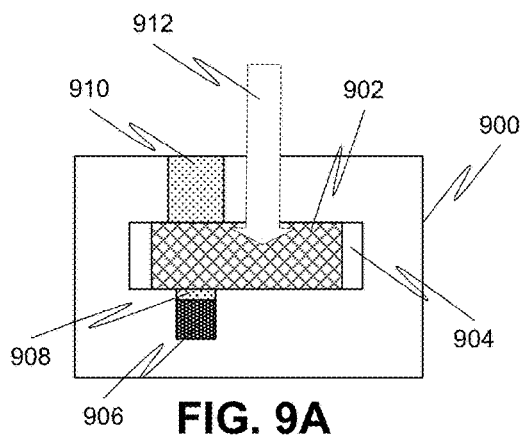
FIGS. 9A-9B are schematic diagrams showing top and side views of another hydrogel MEMS device for drug delivery in a first configuration, according to one or more embodiments of the disclosed subject matter.
Figure 9B:
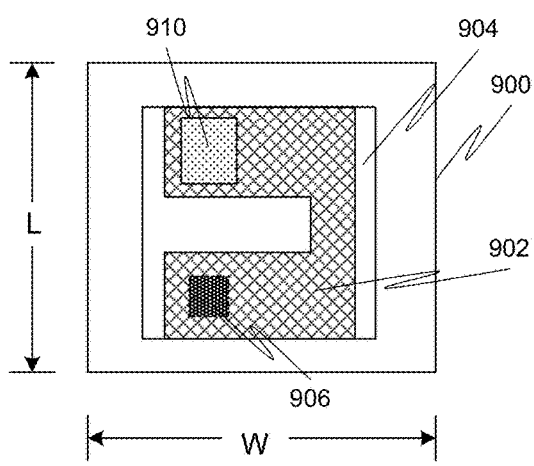

The exposed portions 724 thus join the slab 722 and the structure 714 together to form a new unitary hydrogel structure 726 with a cavity 728 contained therein, as shown in FIG. 7D. For example, structure 726 may form a box having dimensions of 10 mm×10 mm×1.1 mm, with a cavity therein of 6 mm×6 mm×0.7 mm. The cavity 728 can be filled with uncrosslinked polymers. In FIG. 7E, a needle 730 can be used to remove the polymers from the cavity 728. The cavity 728 can subsequently be filled with a drug or a drug surrogate using needle 730. The hydrogel structure 726 can then be incubated, for example, in PBS at 37° C. under gentle agitation for 30 days, to measure diffusion of the drug or drug surrogates out of the cavity.

In experiments, the permeability of fabricated hydrogel constructs was characterized by using entrapped dextran solutions of various molecular weights within different compositions of hydrogel. Diffusion out of the hydrogel was measured over time after incubation at 37° C. in PBS. The cumulative amount of dextran that escapes the hydrogel was measured after a period of about 30 days. The amount of dextran that diffuses out of the hydrogel construct is a result of the permeability of the hydrogel as well as any imperfections in the construct resulting from the fabrication process. The baseline diffusion of dextran out of the most impermeable gel may be reflective of the limit of the fabrication process. Results of such testing indicate a minimal baseline diffusion of 6.0±0.9% for the combination of 4k400 hydrogel and 155 kDa dextran.

Testing was performed to ascertain the diffusion of FITC-labeled dextran (150 kDa) that was polymerized in PEGDA gels (10% of 10 kDa PEGDA) with and without encapsulation within 4K400 PEGDA gels (PEGDA gel composite consisting of 10% of 4 kDa PEGDA and 5% 400 Da PEGDA). Results demonstrate that 4K400 PEGDA gels successfully block the diffusion of dextran even after 4 weeks while 10K10 PEGDA gels are permeable to dextran.

Fluorescence recovery after photobleaching (FRAP) experiments were performed to obtain the diffusion coefficient of the gels. FITC-conjugated dextran with molecular weights of 3 kDa, 20 kDA, and 155 kDa were used. The gels of interest were first polymerized on trimethoxysilyl methacrylate (TMSM) treated glass slides using 5 mm×5 mm photomasks, which thereby ensures that the hydrogel adheres to the glass slide and does not move during imaging. The polymerized gel was then immersed in solutions of FITC-conjugated dextran. After overnight incubation, the gels were rinsed of excess FITC-dextran with PBS and FRAP was performed on the gels using a multiphoton confocal microscope. An argon laser was used to form a bleached region on the gel (95% power) as well as to image (6% power) the gel. A 1-D diffusion model was used to approximate the associated diffusion coefficient.

In order to characterize the permeability of the fabricated hydrogel constructs, dextran solutions of various molecular weights were entrapped within different compositions of hydrogel. The diffusion of the dextran solutions out of the hydrogel was measured over time after incubation at 37° C. in PBS. A 10 mm×10 mm×1.1 mm cube with an inner void measuring 6 mm×6 mm×0.7 mm was fabricated out of the hydrogel of interest. These constructs were punctured with a 21G needle at an angle of 50° and left in PBS overnight to allow for the diffusion of uncrosslinked prepolymer out of the construct as well as for the hydrogel to swell and seal the punctured site. In order to fill the constructs with dextran (3 kDa, 20 kDa and 155 kDa, conjugated with Tetramethyl Rhodamine Isothiocyanate (TRITC)), a 32G needle was attached to a micropipette to inject 14 μL of 20 μg/mL of TRITC-dextran solution.

For in vivo demonstration of drug delivery within a disease model, each chamber can be individually loaded with Herceptin® (trastuzumab) during the device fabrication process. Herceptin® (trastuzumab) is used to treat early stage breast cancer that is Human Epidermal growth factor Receptor 2-positive (HER2+). It is typically delivered intravenously once every 1-3 weeks depending on the treatment regime of the patient. Treatments using Herceptin® (trastuzumab) typically last up to 52 weeks (17-52 doses), resulting in discomfort to the patients. Injections of large-volumes, such as those volumes used in treatment with Herceptin® (trastuzumab), can cause pain, discomfort, distortion to the surrounding tissue, irritation and edema. However, in vivo studies have suggested that cancer therapy using Herceptin®

(trastuzumab) can yield results after just 3 weeks of treatment with twice weekly doses. Although the use of Herceptin® (trastuzumab) in the hydrogel MEMS device has been described herein, embodiments of the disclosed subject matter are not limited to this drug. Rather, embodiments of the disclosed subject matter can be used with a variety of other drugs according to one or more embodiments of the disclosed subject matter. For example, the implantable MEMS device can be loaded with other small molecule drugs used in the treatment of cancer, such as, but not limited to, doxorubicin and paclitaxel.

An embodiment of a hydrogel MEMS device 800 for drug delivery is shown in FIGS. 8A-8D. The device 800 can include multiple chambers 810, each having a single "dose" of a drug for in vivo delivery to a patient. Drug delivery may be controlled by an iron-doped hydrogel piece 806 that can be magnetically actuated to slide to open/close individual chambers 810 for on-demand dosing. For example, each chamber 810 can have a volume of approximately 5004 and can contain about 0.1 mg of a desired drug, which is comparable to the in vivo dosing of Herceptin® (trastuzumab) in mouse cancer models.

When a dose is released due to the displacement of the iron-loaded plug 806 along channel 802, the drug can migrate from the chamber 810 via path 812 to a diffusion window 804 in the channel. For example, the diffusion window may be a hydrogel of different composition as compared to the bulk material of the device 800. The diffusion window 804 can allows small molecules (e.g., less than 150 kDa) to diffuse across it.

The shape of the iron-loaded hydrogel plug 806 may be complementary to the shape of the main parent channel 802 in which it moves. Such a design may allow for step-wise control of the iron-loaded plug 806, such that it only releases one dose when exposed to a magnetic field for a given period of time (e.g., one dose for 4 second exposure). Various parameters may affect the step-wise movement of the iron-loaded hydrogel plug 806. In general, the PEGDA hydrogels (for example, 4k400 gels) can be doped with 30% (v/v) iron nanoparticles, but higher doping concentrations with iron nanoparticles may result in iron-plugs that respond stronger/faster to magnetic actuation. However, beyond a certain concentration (e.g., 50% v/v), the hydrogel may fail to fully polymerize due to increased opacity at higher doping concentrations. Doping concentration may be maintained below 40% for the iron-loaded hydrogel plugs in order to allow adequate polymerization and actuation speed/strength.

A stiffness "mismatch" between the "bump" on the iron plug and the channel in which the iron plug travels may be necessary such that the iron plug can move from notch-to-notch. A less stiff material (for example, 10k10 or 10k5 gels) compared to the notch and/or the plug (for example, 4k400 gel with 30% or 60% iron nanoparticles) may be used for the bump on the iron plug.

The geometry of the bump 808 on iron-loaded plug 806 can also affect the step-wise movement of the iron-loaded hydrogel plug. Interaction of bump 808 with notches 814 at the end of paths 812 can encourage incremental motion of the plug 806 in the channel 802. In addition, the bump-notch interaction may serve to retain the plug 806 at a location until subsequent magnetic actuation as so to prevent inadvertent or undesired motion. An additional notch 816 may be provided along the channel 802 at a fully open location of device 800.

The notches 814/816 and/or the bump 808 can be fabricated so as to have a semicircular or arcuate configuration, which may assist in the ability of the plug 806 to move from notch 814/816 to notch 814/816. Bumps that protrude 0.15 mm and 0.2 mm out from the edge of the rectangular iron-plug may be too small since the iron plug may move freely without fitting into the notches. Bumps that protrude 0.3 mm out from the edge of the rectangular iron-plug may have the best success rate for moving notch-to-notch. Alignment of the layers forming the various hydrogels during fabrication thereof can have an effective on the performance of the bump/notch configuration. Changing the aspect ratio of the bump, using different shapes (e.g., an oval-shaped bump that is taller than it is wide) and more flexible materials (e.g., PEGDA20k) may help address these issues.

A fabricated hydrogel MEMS device 800 can carry, for example, 6 doses for drug delivery, as shown in FIGS. 8A-8D. However, fewer or additional doses are also possible according to one or more contemplated embodiments. In addition, since the drug-loaded chambers 810 are isolated from each other, the different chambers 810 can be used for delivery of more than one type of drug, for example, in cases of combination therapy. Embodiments of the disclosed hydrogel MEMs devices and other hydrogel MEMS devices fabricated according to the disclosed methods and techniques can have the flexibility of delivering multiple types of drugs/biologics, can be designed to suit different treatment regimens (single drug treatment, combinational therapy, etc.), and can show a longer sustained functionality after implantation. Embodiments of the movable component in a hydrogel MEMS device can be isolated within the device and can be actuated as long as the exterior bulk material is present.

Each chamber 810 can be loaded with a particular drug, drug model (e.g., 150 kDa dextran), or other desired chemical. For example, dextran molecules can be labeled with FITC or TRITC and have similar molecular weight as Herceptin® (trastuzumab). In actual use, the chamber 810 is loaded with one or more drugs of interest to be delivered in vivo to the patient. For example, each chamber can contain a single dose of the intended drug (trastuzumab). The intended drug or drug model can be suspended in gel and polymerized into "squares" prior to assembling the entire drug delivery device. These "squares" are then loaded into the chambers of the device during the fabrication process to form individual depots of drug. At the same or different time in the fabrication process, a pre-fabricated hydrogel plug that is doped with superparamagnetic iron nanoparticles can also loaded into the device for use as the remote actuation hydrogel component, the operation of which is described elsewhere herein.

Additional remote actuation methodologies for an all hydrogel MEMS device are also possible according to one or more contemplated embodiments. In general, externally applied wave energy (i.e., electromagnetic wave, magnetic fields, and/or sound waves) can be used to cause actuation of a hydrogel component within the hydrogel MEMS device. Such actuation may allow for the release of a drug for delivery to a patient in vivo. For example, the hydrogel component can be doped with nanoshells, carbon nanotubes, or other nanoparticles. Infrared radiation (e.g., NIR) applied to the MEMS device can generate heat that causes actuation of the doped hydrogel component. In another example, the hydrogel component can include a thermally sensitive polymer (e.g., coating of N-isopropylacrylamide (NIPAAm)). High intensity focused ultrasound (HIFU) can be focused on the device or the component therein to cause a temperature increase at the focus, thereby causing actuation of the hydrogel component. Due to the high penetration depth of the ultrasound this technique allows actuation of devices implanted deeper in the host body. These polymers can also be micropatterned into sophisticated implanted medical devices. Overall, this material enables the development of medical devices which can be non-invasively manipulated even after host implantation. Applications include drug delivery, implantable sensors, and assistance with noninvasive surgery. In any of the embodiments, other thermally sensitive polymers may also be used, for example, poly (N-isopropylacrylamide-co-acrylamide) (NiPAAm-co-AAm).

The use of ultrasound for in vivo of an implanted hydrogel MEMS devices may have additional advantages as well. For example, HIFU can enhance diffusion. Thus, the use of HIFU in combination with drug delivery using the MEMS device may increase the penetration of drugs into a particular tissue. In addition, the actuation methods may be combined to provide a safety factor with regard to inadvertent drug delivery. Thus, the presence of a single actuation field would be insufficient to cause release of the drug, but providing both actuation fields would allow drug release. For example, HIFU can be used to alter a shape of a movable plug to allow it to be moved by a magnetic field, which plug would otherwise be immovable without the HIFU application (see FIGS. 12A-12D).

Figure 10A:
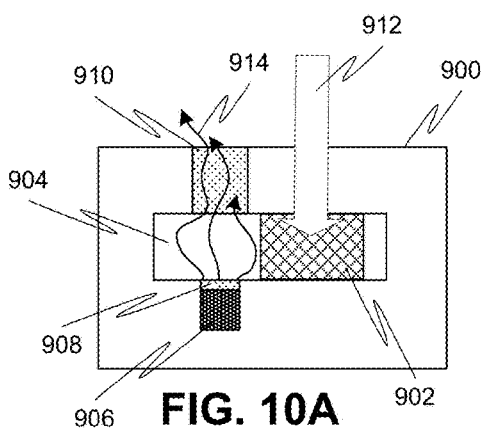
FIGS. 10A-10B are schematic diagrams showing top and side views of another hydrogel MEMS device for drug delivery in a second configuration, according to one or more embodiments of the disclosed subject matter.
Figure 10B:
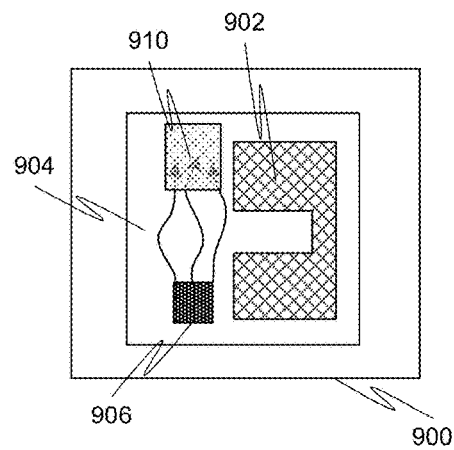

Referring to FIGS. 9A-10B, a simplified example of a HIFU actuated hydrogel MEMS device 900 for drug delivery is shown. The hydrogel MEMS device 900 has an unbroken shape and can have a structure forming a channel region 904 therein. A thermally responsive hydrogel component 902, for example, a hydrogel plug, having an unbroken U-shape can be enclosed within the channel region 904 and capable of independent motion therein. Accordingly, the movable hydrogel plug 902 can move within channel 904. Active remote actuation of the plug 902 can be achieved including a thermally responsive gel (e.g., a coating or incorporation of N-isopropylacrylamide (NIPAAm)) into the hydrogel plug 902. Remote control of the location of the plug 902 is thus accomplished by heating the plug 902 by applying HIFU 912 via an ex vivo ultrasound actuation setup. Heating of the hydrogel plug 902 by HIFU 912 causes the plug 902 to shrink in shape, thereby allowing access to channel 904 by reservoir 906 as shown in FIGS. 10A-B.

A drug can be contained in a reservoir 906 in the hydrogel MEMS device structure 900. The hydrogel regions bounding the reservoir 906 can have a permeability and/or stiffness designed to contain the drug therein. The drug may leave the reservoir 906 via an outlet portion 908 arranged adjacent to channel 904. For example, the outlet portion 908 can be a hydrogel region having a permeability that readily allows diffusion of the drug therethrough. Alternatively, the outlet portion 908 may be an opening formed in the hydrogel structure 900 adjacent the channel 904. Thus, the drug in the reservoir 906 can enter the channel 904 via the outlet portion; however, in FIGS. 9A-9B, the location of plug 902 in the channel 904 blocks egress of the drug from the reservoir. The change in the shape of the plug 902 retracts the plug 902 along the channel to a location where the outlet portion 908 of the reservoir 906 is unblocked, so as to allow diffusion 914 of the drug out of the reservoir 906. The drug thus enters the channel 904, where it can exit device 900 via a diffusion window 910, similar to the embodiment of FIGS. 1A-2B.

Figure 11:
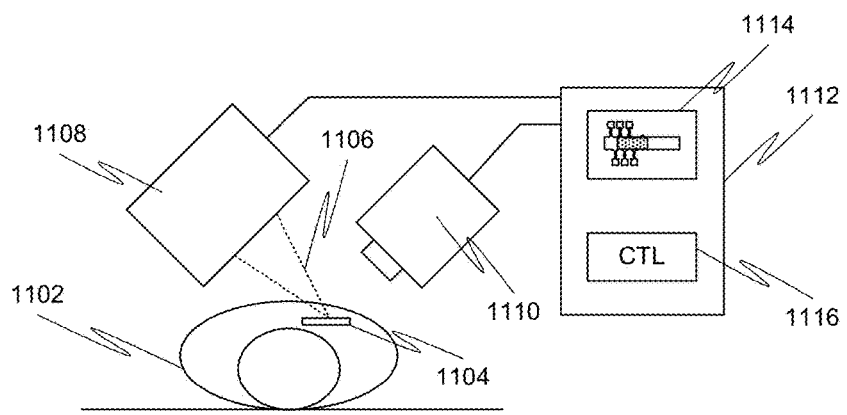
FIG. 11 is a schematic diagram showing a system for in vivo actuation of a hydrogel MEMS device for drug delivery, according to one or more embodiments of the disclosed subject matter.

Referring to FIG. 11, a hydrogel MEMS device 1104 according to one or more embodiments of the disclosed subject matter is shown implanted in a patient 1102. The MEMS device 1104 may be constructed to deliver one or more drugs at a desired location in the body of the patient 1102. An imaging device 1110 can be used to image the device 1104 within the patient so as to view the hydrogel component (e.g., plug 102 or 902) during or after actuation. A computer 1112 may provide real-time or near real-time imaging to a user, such as medical personnel administering the desired drug treatment. Accordingly, the user may visually verify displacement of the hydrogel component and delivery of a desired drug dose. Computer 1112 may have other input/output capability for interacting with the user. Computer 1112 can include a control module 1116, which may control operation of the imaging device 1110 and reconstruction of image 1114. In addition, ex vivo actuation device 1108 can be provided for providing external wave energy (e.g., HIFU, magnetic field, or NIR) to the device 1104 within the patient 1102 for causing actuation of the hydrogel component within the device 1104 to release a drug dose. Computer 1112 and/or control module 1116 can also control operation of the actuation device 1108. Although shown as separate components, it is contemplated that one or more of the actuation device 1108, the imaging device 1110, and the computer 1112 may be integrated into a single unit.

In FIGS. 12A-12D, an implantable hydrogel MEMS device 1200 that employs two wave energy applications in order to actuate the hydrogel component therein is shown. Device 1200 can have a chamber 1202 that contains a drug to be delivered. As with other configurations described herein, the drug may be retained in the chamber 1202 and can escape by the device 1200 through a diffusion window located at some portion of a channel 1204. A thermally responsive hydrogel component 1208 can be arranged in portion 1206 that blocks egress of the drug from chamber 1202. In addition, the hydrogel component 1208 can conform to the size of the channel portion 1206, which thereby prevents its motion along channel 1204.

Figure 12A:
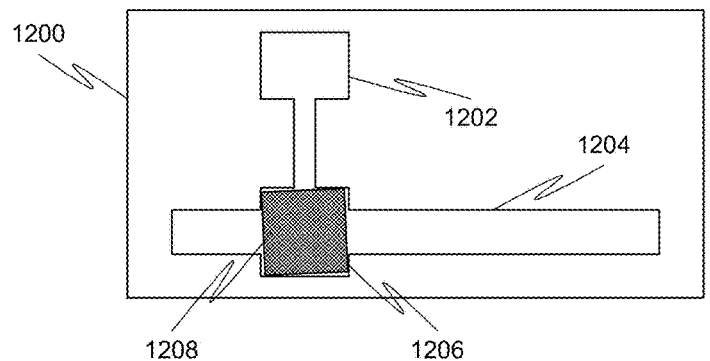
FIGS. 12A-12D are schematic diagrams showing a top view of a remotely actuated hydrogel MEMS device for drug delivery during different stages of actuation, according to one or more embodiments of the disclosed subject matter
Figure 12B:
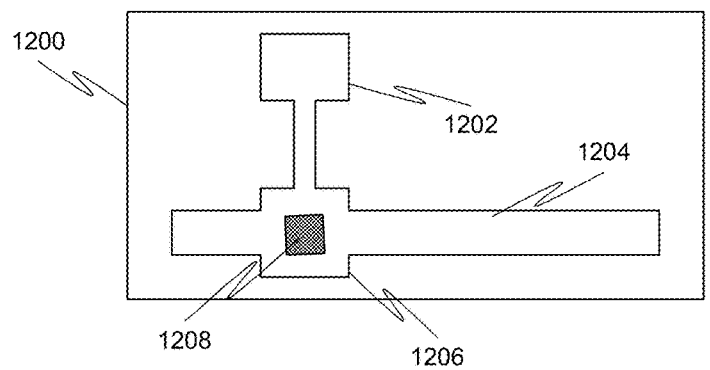
Figure 12C:
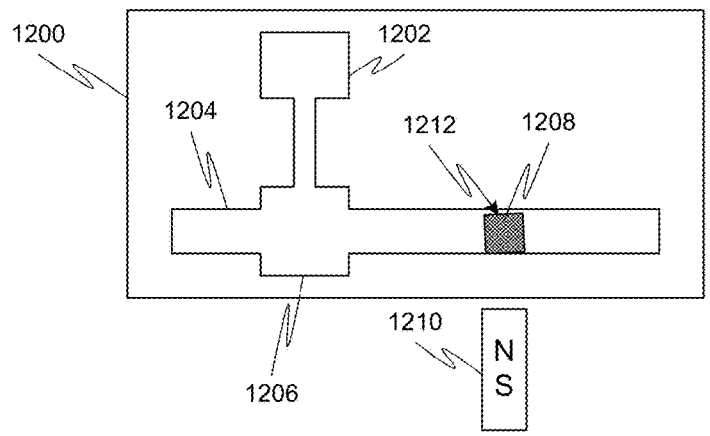
Figure 12D:
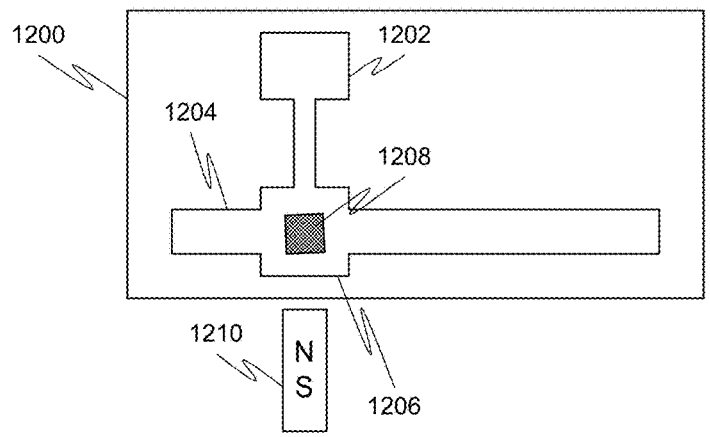

The hydrogel component 1208 can be doped with magnetic nanoparticles and can be coated with a thermo-responsive gel (e.g., NiPAAm). At body temperature the NiPAAm will be swollen in its equilibrium state, thereby locking the plug in one fixed position at channel portion 1206. Application of HIFU in FIG. 12B heats the component 1208, such that the NiPAAm hydrogel plug 1208 shrinks. Application of a magnetic field in FIG. 12C, for example, using magnetic 1210, can move the plug 1208 along channel 1204 to a position 1212 where the chamber 1202 is completely unblocked. The drug can thus be released from the chamber for delivery to the patient via a diffusion window (not shown) along channel 1204. After drug delivery is complete (for example, after a sufficient time has elapsed), the plug 1208 can be returned to region 1206, as shown in FIG. 12D. Removal of the HIFU results in a decrease in temperature of the plug 1208, which causes the plug 1208 to swell back to the original shape and configuration of FIG. 12A.

In FIGS. 13A-13D, an implantable hydrogel MEMS device that employs two wave energy applications in order to actuate the hydrogel components therein is shown. A drug can be contained in cavity 1304 formed by hydrogel structure 1302. An iron-doped hydrogel plug 1310 can seal the hydrogel structure 1302 at one end of the cavity 1304 while thermally responsive hydrogel 1306 seals the other end of the cavity. Additional thermally responsive hydrogel 1308 may be provided between plug 1306 and the hydrogel structure 1302, whereby frictional contact between the hydrogels 1302, 1306, 1308 restricts motion of the plug 1306.

Figures 13A, 13B, 13C, 13D:
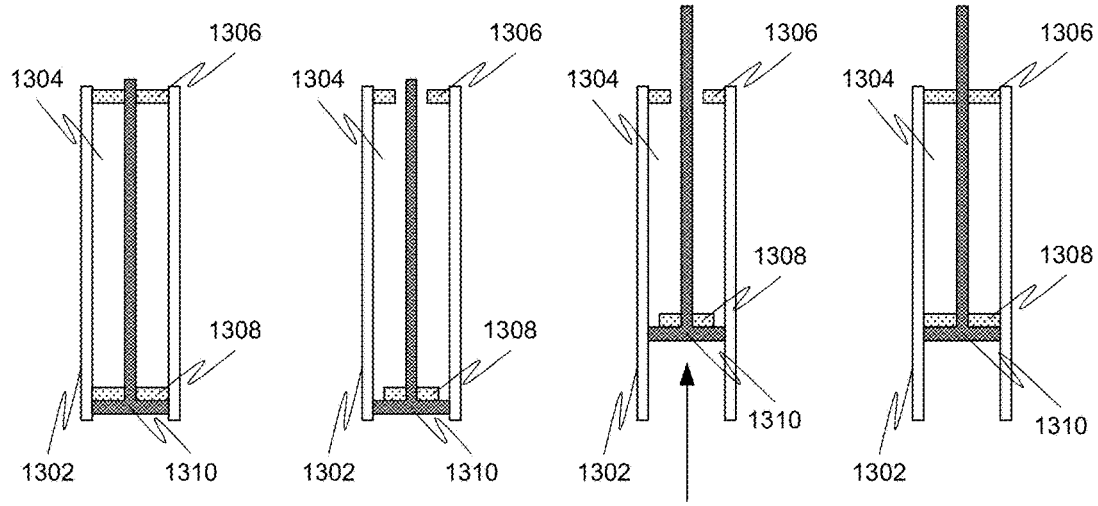
FIGS. 13A-13D are schematic diagrams showing a side view of a remotely actuated hydrogel MEMS device for drug delivery during different stages of actuation, according to one or more embodiments of the disclosed subject matter

Application of HIFU in FIG. 13B causes heating of the thermally responsive hydrogels 1306, 1308 (e.g., to a temperature in excess of 43° C.). As a result, the thermally responsive hydrogels shrink in size. Hydrogel 1306 retracts at the end of the cavity 1304, thereby providing an opening through which drug contained in the cavity can leave the hydrogel structure. At the same time, hydrogel 1308 retracts from the hydrogel structure 1302, thereby allowing the plug 1310 to move freely within hydrogel structure 1302. Application of a magnetic field in FIG. 13C causes the plug 1310 to displace along the hydrogel structure and dispensing a volume of the drug from an open end of the cavity 1304. Withdrawing the HIFU in FIG. 13D allows the thermally responsive hydrogels to return to their original size, thereby locking the plug 1310 in a new position in the cavity 1304 and once again sealing the cavity. Thus, a controlled volume of the drug may be dispensed from the cavity.

Figures 14A, 14B:
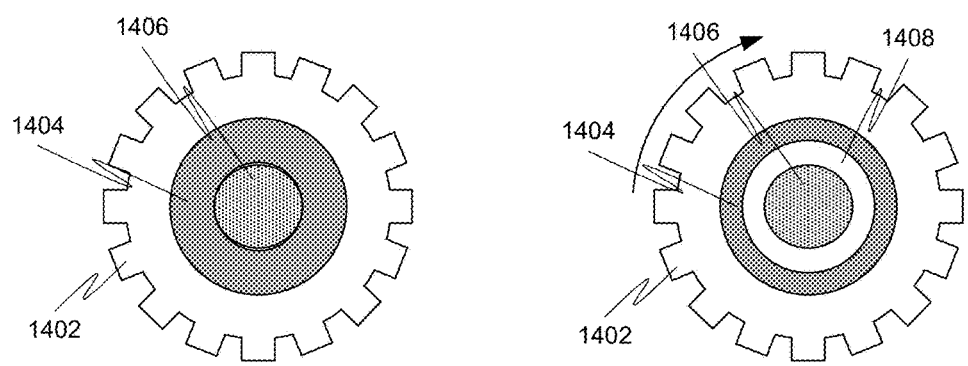
FIGS. 14A-14B are schematic diagrams illustrating components of a rotatable hydrogel MEMS device without and with application of high intensity focused ultrasound, respectively, according to one or more embodiments of the disclosed subject matter.

In one or more embodiments of the disclosed subject matter, thermally responsive hydrogels can be used to restrict and regulate motion of magnetically actuatable hydrogels, for example, to further safety or control a dispensing amount. In another example configuration shown in FIGS. 14A-14B, a thermally responsive hydrogel can regulate rotational motion of a hydrogel microgear. Hydrogel gear 1402 can include magnetic particles therein and can be arranged to rotate about hub 1406. A thermally responsive material 1404 can be radially disposed between the hub 1406 and the gear 1402. Without application of HIFU, the thermally responsive hydrogel 1404 impacts the hub 1406 such that rotational motion of the gear 1402 is impeded upon application of a magnetic field, as shown in FIG. 14A. Application of the HIFU in FIG. 14B causes the hydrogel 1404 to shrink away from the hub 1406, thereby allowing the gear 1402 to rotate freely. Application of HIFU may thus allow remote start and stop control of a hydrogel gear.

Figure 15A:
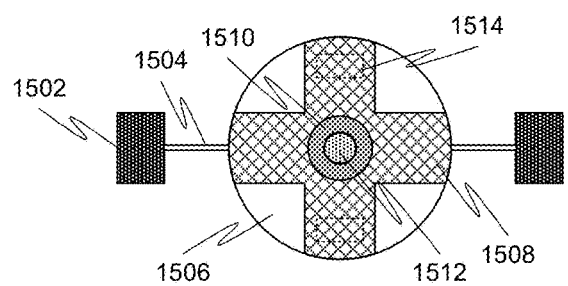
FIGS. 15A-15E are schematic diagrams showing a top view of a rotatable hydrogel MEMS device during different stages of actuation, according to one or more embodiments of the disclosed subject matter.

In addition, the use of HIFU with thermally and magnetically responsive hydrogels can allow for regulation of a volume of drug or other substance to be delivered through a diffusion window of the device. FIGS. 15A-15F show operation of such a device. In FIG. 15A, hydrogel gear 1508 is doped with magnetic particles so as to be actuatable by a magnetic field while a thermally responsive hydrogel 1510 is provided between hub 1512 and gear 1508 in a radial direction. The gear 1508 can be disposed within a circular channel of the hydrogel MEMS device. Diffusion windows 1514 can allow diffusion of molecules from the channel to an exterior of the MEMS device. Reservoirs 1502 can be connected to the channel by flowpaths 1504, which are blocked by gear 1508 in FIG. 15A.

Figure 15B:
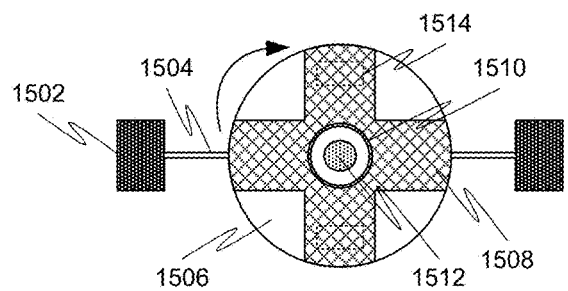
Figure 15C:
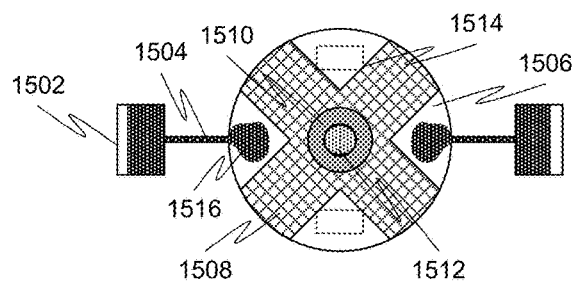
Figure 15D:
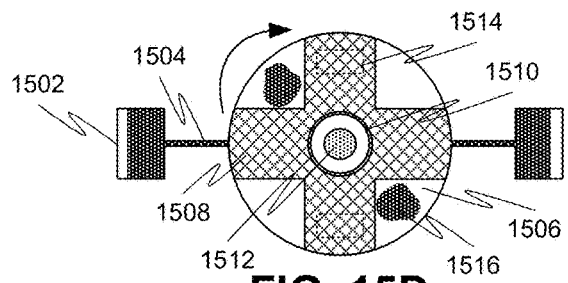
Figure 15E:
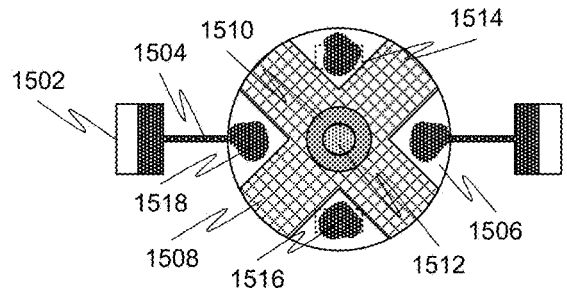

In FIG. 15B, HIFU is applied to the device, thereby causing thermally responsive hydrogel 1510 to shrink from hub 1512. Gear 1508 is thus free to rotate about hub by magnetic actuation. Application of the HIFU and magnetic fields may be synchronized such that the gear 1508 is only capable of displacing an incremental distance before return of hydrogel 1510 to its original shape ceases motion of the gear 1508. Diffusion from chamber 1502 may provide a portion 1516 of drug in isolated regions 1506 in the channel. Thus, the volume of drug to be delivered can be regulated using the isolated regions 1506. Further synchronized application of the HIFU and magnetic fields may allow displacement of gear 1508 to the position shown in FIG. 15D, where portions 1516 can be held until needed for delivery. In FIG. 15E, gear 1508 can be further rotated to allow delivery of portions 1516 through diffusion windows 1514, while additional drug portions 1518 are loaded into regions 1506 of channel. Discrete portions of the drug can thus be delivered at regulated intervals.

A thermo-responsive material for drug delivery that can be actuated by HIFU provides high localization specificity and providing multiple drugs implanted in the same device but released separately when needed. The system allows for controlled drug release over several days by increasing the temperature above physiological levels. A temperature-responsive hydrogel is actuated ("squeezed") when heat energy is supplied externally by HIFU, causing the hydrogel to shrink and the encapsulated drug to be squeezed out to the surrounding area. Controlling the intensity and duration of applied heat allows precise metering of the drug delivered. The drug delivery system is made of poly (N-isopropylacrylamide-co-acrylamide) (NiPAAm-co-AAm)—a temperature-responsive polymer, i.e., the gel shrinks when experiencing an increase in temperature. This effect takes advantage of the thermodynamically favorable bonding at different temperatures. At lower temperatures the polar groups in NiPAAm-co-AAm make favorable hydrogen bonds with water, and thus the hydrogel is in a swollen state. When the temperature increases, the higher energy state makes these interactions less favorable and makes polymer-polymer and water-water interactions more favorable. This causes the water molecules to diffuse from the hydrogel and the polymer chains to collapse onto themselves forming hydrophobic interactions. NiPAAm-co-AAm is highly temperature sensitive as is known. NiPAAm-co¬ AAm gels may be created to with selected size, shape, and other features by micro-patterning using UV-photolithography, molding, or other techniques. The thermo-sensitive properties of NiPAAm-co-AAm, i.e., the temperature when the gel starts to contract, can be changed by altering the ratio of NiPAAm: AAm in the gel. In embodiments, the gel composition is optimized for actuating drug release between normal and mild-hyperthermia body temperatures based on a selected mechanical configuration of the device.

The tendency of drugs to diffuse through NiPAAm-co-AAm gels into the surrounding tissue is prevent when the gel is not actuated. This feature may be provided, in embodiments, by encasing a hydrogel matrix, for example, NiPAAm-co-AAm, inside a low permeability capsule which is not of the same temperature sensitivity as the encased hydrogel. For example, the capsule may be one which is biocompatible and absorbed by the body after a time such as a hydrogel. Alternatively, if it can be recovered, it may be of inert material such as polydimethylsiloxane (PDMS). The capsule may have releasing holes, for example two holes that prevent bulk diffusion during non-actuation periods, but which allow for drug diffusion when the gel is actuated. The capsule may be of a hydrogel material having reduced permeability. Instead of a temperature-sensitive hydrogel inside the capsule (hydrogel or other material), the internal hydrogel could have magnetic material that changes the shape or size of the hydrogel material inside causing release of the material inside the capsule. The capsule can have a permeable window instead of holes in further embodiments. In other embodiments, a time-varying magnetic field may cause oscillatory disturbance of the internal material-carrying hydrogel element that increases the rate of release. The oscillating field may be generated using an AC current in a coil positioned outside the body of a patient.

In embodiments, a hydrogel is fabricated according to any of the disclosed methods and systems, for example, NiPAAm-co-AAm may be fabricated by UV photo-polymerization. In an example embodiment, a pre-polymer solution mixture, containing NiPAAm (1.7 M, 20% w/w), the co-monomer AAm (85:15 molar NiPAAm:AAm), the cross-linker MBAAm (5% w/w respect NiPAAm monomer) and the photoinitiator 2-hydroxy-2-methyl-1-phenyl-propan-1-one (Darocur-1173) (0.1% w/w), are dissolved in EtOH: water (50:50 v/v) and placed inside a container with a selected thickness and covered by a transparent cover such as glass plate. A photo-mask transparency with a selected design may be placed over the glass slide and the photopolymerization initiated by irradiating with UV light, for example 350 nm. After polymerization a small hydrogel resulting from the polymerization may be rinsed to remove non-crosslinked pre-polymer and allowed to swell to equilibrium at room temperature in deionized water. The hydrogel may be dried and stored at room temperature until use.

The capsule may be made by molding a shell material, such as PDMS, and forming one or more small holes, by machining, punching or molding. The capsule may be made of two shell parts that can be bonded together to for a sealed volume. The dried gel may be placed in sealed volume and enclosed by bonding the shell parts. The latter may then be stored until use. Before using the device, the capsule may be filled with water through one or both of the release holes which will cause the gel to swell until it occupies the entire internal volume. The capsule internal volume dimensions may be selected to be smaller than the equilibrium volume of the hydrogel at body temperature such that, once implanted, the release holes of the capsule are mechanically sealed by the swollen gel against the container walls, minimizing the diffusion of the drug. When the hydrogel is actuated, for example by HIFU, the gel shrinks releasing the drug inside the capsule such that it diffuses out to the external media through the releasing holes. The activated state may be terminated to reduce the diffusion of drug by reducing the gel temperature whereupon it expands back to the hole-sealing state.

In one or more embodiments of the disclosed subject matter, an implantable MEMS device for delivery of a substance in vivo can include a first hydrogel structure and a second hydrogel structure. The first hydrogel structure can have a reservoir containing the substance therein. The reservoir can have an outlet portion. The second hydrogel structure can be retained within the first hydrogel structure and can block the outlet portion to prevent egress of the substance from the reservoir. The second hydrogel structure can include a temperature responsive polymer that causes the second hydrogel structure to change shape upon application of high intensity focused ultrasound so as to unblock the outlet portion, thereby allowing egress of the substance from the reservoir.

In one or more embodiments of the disclosed subject matter, the first hydrogel structure can be constructed to maintain its shape upon the application of the high intensity focused ultrasound. The temperature responsive polymer can include N-isopropylacrylamide (NIPAAm). The first and second hydrogel structures can include polyethylene glycol (PEG). The outlet portion can be a region of the first hydrogel structure having a different permeability than other regions of the first hydrogel structure bounding the reservoir. The outlet portion can be one of a diffusion window and an opening in the first hydrogel structure. The second hydrogel structure can include magnetic particles embedded therein. The second hydrogel structure can be doped with iron nanoparticles. At least one of the first and second hydrogel structures is seeded with cells for in vivo or ex vivo tissue growth. The substance can be one of a chemical, cells, particles or nanoparticles, and nanorobots. The substance can be a drug.

In one or more embodiments of the disclosed subject matter, the second hydrogel structure can be disposed in a channel of the first hydrogel structure. Prior to the second hydrogel structure changing shape, walls of the channel can restrict motion of the second hydrogel structure along the channel, and after the change in shape, the second hydrogel structure is free to move along the channel. The second hydrogel structure can be constructed to be displaced along the channel by a magnetic field while the high intensity focused ultrasound is applied thereto and to be held in place by walls of the channel despite the magnetic field when high intensity focused ultrasound is not applied thereto.

In one or more embodiments of the disclosed subject matter, the implantable MEMS device can also include a third hydrogel structure disposed in the reservoir with the substance. The third hydrogel structure can include magnetic particles therein. The third hydrogel structure can be constructed to displace upon application of a magnetic field so as to dispense the substance through the outlet portion.

In one or more embodiments of the disclosed subject matter, an implantable MEMS device formed of hydrogels can include first and second hydrogels. The second hydrogel can be separate from the first hydrogel and supported thereon. The second hydrogel can be displaceable independent of the first hydrogel. The second hydrogel can be doped with magnetic particles and coated with a thermally responsive polymer such that application of high intensity focused ultrasound to the MEMS device causes a change in shape of the second hydrogel and such that application of a magnetic field to the MEMS device causes displacement of the changed shape second hydrogel with respect to the first hydrogel.

In one or more embodiments of the disclosed subject matter, the first hydrogel can include a channel with the second hydrogel supported therein. The second hydrogel can have an initial shape prior to the high intensity focused ultrasound application that retains the second hydrogel in a portion of the channel. The second hydrogel can have a changed shape during the high intensity focused ultrasound application that allows the second hydrogel to move along the channel. The first hydrogel can include one or more reservoirs holding a chemical and/or particles therein. The second hydrogel can be constructed to move from a first position preventing egress from the one or more reservoirs to a second position allowing egress from the one or more reservoirs. The chemical can be one of a drug and a growth factor, and the particle can be one of cells, nanorobots, and nanoparticles. The first and second hydrogels can each have a thickness in a direction perpendicular to a plane in which the second hydrogel moves. The second hydrogel thickness can be less than the first hydrogel thickness. The first and second hydrogels can include polyethylene glycol (PEG), and the thermally responsive polymer can include N-isopropylacrylamide (NIPAAm).

In one or more embodiments of the disclosed subject matter, an implantable MEMS device method can include directing high intensity focused ultrasound at the MEMS device so as to increase a temperature thereof. The increased temperature can cause a thermally responsive hydrogel component housed in a hydrogel structure of the MEMS device to change shape. The method can further include directing a magnetic field at the MEMS device to cause displacement with respect to the hydrogel structure of the thermally responsive hydrogel component or another hydrogel component housed in the hydrogel structure.

In one or more embodiments of the disclosed subject matter, the thermally responsive hydrogel component can have magnetic particles embedded therein and can be displaced by the magnetic field. The displacement can allow diffusion of a substance from a reservoir of the hydrogel structure. The substance can be at least one of a chemical, cells, and particles. The substance can be a drug. The another hydrogel component can have magnetic particles embedded therein and can be displaced by the magnetic field. The displacement of the another hydrogel component can eject a substance from a reservoir of the hydrogel structure. The thermally responsive hydrogel can return to its original shape after the directing high intensity focused ultrasound ceases. The thermally responsive hydrogel can include polyethylene glycol (PEG) and N-isopropylacrylamide (NIPAAm).

In one or more embodiments of the disclosed subject matter, the method can further include forming at least one of the hydrogel structure and the thermally responsive hydrogel component using flow through layer-by-layer UV photolithography. The thermally responsive hydrogel component can be inserted into the hydrogel structure. A reservoir in the hydrogel structure can be loaded with one of a chemical and particles. The directing the magnetic field can cause displacement allows egress of contents of the reservoir therefrom. Prior to the directing the magnetic field but after the loading, the device can be implanted in a patient. The contents of the reservoir can include a drug to be delivered to the patient. The directing the magnetic field to cause displacement can allow delivery of the drug from the reservoir to the patient in vivo.

In one or more embodiments of the disclosed subject matter, an implantable MEMS device for delivery of a substance in vivo can include a first hydrogel structure and a second hydrogel structure. The first hydrogel structure can have at least one outlet portion in a wall thereof and an internal enclosed volume. The second hydrogel structure can be retained within the first hydrogel structure enclosed volume. The second hydrogel structure can have a substance therein such that when said second hydrogel structure shrinks, the substance exits the second hydrogel structure. The second hydrogel structure can include a temperature responsive polymer that causes the second hydrogel structure to shrink upon application of high intensity focused ultrasound thereby allowing egress of the substance from the first hydrogel at least one outlet portion.

In one or more embodiments of the disclosed subject matter, the first hydrogel structure can be constructed to maintain its shape and size upon the application of the high intensity focused ultrasound. The temperature responsive polymer can include at least one of N-isopropylacrylamide (NIPAAm) or (N-isopropylacrylamide-co-acrylamide) (NiPAAm-co-AAm). The first and second hydrogel structures can include polyethylene glycol (PEG). The at least one outlet portion can include a permeable region of the first hydrogel structure. The first hydrogel structure can have a lower permeability than the second hydrogel structure. The outlet portion can be one of a diffusion window and an opening in the first hydrogel structure.

In one or more embodiments of the disclosed subject matter, an implantable MEMS device for delivery of a substance in vivo, can include a first hydrogel structure and a second hydrogel structure. The first hydrogel structure can have at least one outlet portion in a wall thereof and an internal enclosed volume. The second hydrogel structure can be retained within the first hydrogel structure enclosed volume. The second hydrogel structure can have a substance therein. The first and second hydrogel structures can be configured such that when a magnetic field is applied, the second hydrogel structure changes its shape and/or size and releases the substance that exits the second hydrogel structure and then exits the first hydrogel structure at at least one outlet portion.

In one or more embodiments of the disclosed subject matter, the second hydrogel structure can include magnetic particles embedded therein. The second hydrogel structure can be doped with iron nanoparticles.

In embodiments, a method for forming a hydrogel MEMS device with movable components can include flowing in a first hydrogel precursor into a microfluidic chamber and selectively polymerizing portions of the first precursor therein; replacing the first hydrogel precursor with at least a second hydrogel precursor in the microfluidic chamber; selectively polymerizing portions of the second precursor in the microfluidic chamber; forming a magnetically responsive hydrogel component; transferring the magnetically responsive component to the polymerized portions of the first and second hydrogel precursors; and sealing the magnetically responsive component and the polymerized portions of the first and second hydrogel precursors with a hydrogel layer.

In addition, excess hydrogel precursors may be extracted after the sealing. In addition, the magnetically responsive hydrogel component may be doped with super-paramagnetic microbeads. In addition, the first and second polymerized precursor portions may be formed on a monolithic hydrogel supporting structure. In addition, a height of the microfluidic chamber can be changed between the flowing and the replacing. In addition, the hydrogel may be PEGDA or other photopolymerizable, biocompatible hydrogels.

In embodiments, a hydrogel MEMS device can include a first hydrogel portion having a first permeability, a first hydrogel portion having a second permeability, a well region for containing a chemical adjacent the second hydrogel portion, a third hydrogel portion movable with respect to the second hydrogel portion and magnetically responsive, wherein the third hydrogel portion is movable from a first position blocking the second hydrogel portion such that the chemical contained in the well region cannot diffuse therethrough and a second position allowing the chemical contained in the well region to diffuse through the second hydrogel portion.

In addition, the hydrogel may be PEGDA or other photopolymerizable, biocompatible hydrogels. In addition, the second hydrogel portion may have a permeability to allow chemicals of approximately 150 kDa to diffuse therethrough. In addition, the third hydrogel portion may be doped with super-paramagnetic microbeads. In addition, the first hydrogel may have a permeability that prevents diffusion therethrough of chemicals of approximately 150 kDa. In addition, the first hydrogel may at least partially surround the well region.

Accordingly, disclosed herein are systems, methods, and devices for fabricating (i.e., micromachining) hydrogel materials (e.g., PEGDA) to construct MEMS devices with externally actuatable moving parts, as well as system, methods, and devices for use of the hydrogel MEMS devices. These hydrogel MEMS devices can be subcutaneously implanted, as they are completely biocompatible and potentially biodegradable.

Although particular configurations have been discussed herein, other configurations can also be employed. Thus, the materials, techniques, and methodologies discussed herein for the hydrogel MEMS device may be extended to other applications in addition to the implantable drug delivery application disclosed herein. For example, a hydrogel MEMS device can be fabricated to deliver any type of therapeutic, combination of therapeutics, growth factors (e.g., for in vivo or in vitro tissue engineering), contrast agents (e.g., in vivo models that are periodically injected with a contrast agent for imaging), particles (e.g., nanoparticles, nanorobots, etc.), cells, etc. A hydrogel MEMS device can be fabricated for other applications as well, such as, but not limited to micro-total-analysis systems (μTAS), microchemical processing systems, and other microfluidic devices.

Furthermore, the foregoing descriptions apply, in some cases, to examples generated in a laboratory, but these examples can be extended to production techniques. For example, where quantities and techniques apply to the laboratory examples, they should not be understood as limiting. In addition, although specific chemicals and materials have been disclosed herein, other chemicals and materials may also be employed according to one or more contemplated embodiments.

Features of the disclosed embodiments may be combined, rearranged, omitted, etc., within the scope of the invention to produce additional embodiments. Furthermore, certain features may sometimes be used to advantage without a corresponding use of other features.

It is, thus, apparent that there is provided, in accordance with the present disclosure, methods, systems, and devices for in vivo delivery using remote actuation of implantable hydrogel MEMS devices. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. An implantable MEMS device for delivery of a substance in vivo, the device comprising:
   a first hydrogel structure having a reservoir containing the substance therein, the reservoir having an outlet portion;
   a second hydrogel structure having a shape retained within the first hydrogel structure and blocking the outlet portion to prevent egress of the substance from the reservoir, wherein
   the second hydrogel structure includes a temperature responsive polymer that changes the shape of the second hydrogel structure from a first unbroken shape to a second unbroken shape upon application of high intensity focused ultrasound so as to unblock the outlet portion.

2. The implantable MEMS device according to claim 1, wherein the first hydrogel structure is constructed to maintain its shape upon the application of the high intensity focused ultrasound.

3. The implantable MEMS device according to claim 1, wherein the temperature responsive polymer includes N-isopropylacrylamide (NIPAAm).

4. The implantable MEMS device according to claim 1, wherein the first and second hydrogel structures include polyethylene glycol (PEG).

5. The implantable MEMS device according to claim 1, the outlet portion of the first hydrogel structure includes a hydrogel material having a different permeability than the first hydrogel structure bounding the reservoir.

6. The implantable MEMS device according to claim 1, wherein the outlet portion is one of a diffusion window and an opening in the first hydrogel structure.

7. The implantable MEMS device according to claim 1, wherein said substance is one of a chemical, cells, particles or nanoparticles, and nanorobots.

8. The implantable MEMS device according to claim 1, wherein at least one of the first and second hydrogel structures is seeded with cells for in vivo or ex vivo tissue growth.

9. The implantable MEMS device according to claim 1, wherein
   the temperature responsive polymer reverts the shape of the second hydrogel to substantially the first unbroken shape after the application of the high intensity focused ultrasound ceases.

10. The implantable MEMS device according to claim 1, wherein the second hydrogel structure includes magnetic particles embedded therein.

11. The implantable MEMS device according to claim 10, wherein the second hydrogel structure is doped with iron nanoparticles.

12. An implantable MEMS device, comprising:
    a first hydrogel structure having a reservoir, a channel, and a diffusion window, the reservoir having an outlet portion, the diffusion window being disposed along a wall of the channel and spaced from the outlet portion; and
    a second hydrogel structure retained within the channel of the first hydrogel structure, the second hydrogel structure including a polymer with a first portion that blocks the outlet portion to prevent egress of a substance from the reservoir and a second portion that blocks the diffusion window, the second hydrogel structure having a U-shape,
    wherein said polymer shrinks from a first configuration to a second configuration in response to application of ultrasound thereto,
    in the first configuration the first and second portions block the outlet portion and the diffusion window, respectively, and
    in the second configuration the outlet portion and the diffusion window are unblocked by the first and second portions, respectively, such that the outlet portion and the diffusion window are in fluid communication via the channel.

13. The implantable MEMS device of claim 12, wherein the second hydrogel structure is retained within the first hydrogel structure such that the first portion of the second hydrogel structure blocking the outlet portion in the first configuration is displaced along the channel by the shrinking.

14. The implantable MEMS device of claim 12, wherein said polymer of the second hydrogel structure comprises N-isopropylacrylamide (NIPAAm).

* * * * *

UNITED STATES PATENT AND TRADEMARK OFFICE
CERTIFICATE OF CORRECTION

PATENT NO. : 9,907,906 B2
APPLICATION NO. : 13/953700
DATED : March 6, 2018
INVENTOR(S) : Olga Ordeig et al.

It is certified that error appears in the above-identified patent and that said Letters Patent is hereby corrected as shown below:

In the Specification

The heading and paragraph at Column 1, Lines 6-13 should read as follows:
--STATEMENT REGARDING FEDERALLY SPONSORED RESEARCH
This invention was made with government support under grant 0747747 awarded by the National Science Foundation. The government has certain rights in the invention.--

Signed and Sealed this
Tenth Day of July, 2018

Andrei Iancu
*Director of the United States Patent and Trademark Office*